United States Patent
Olesik et al.

(10) Patent No.: US 9,610,562 B2
(45) Date of Patent: Apr. 4, 2017

(54) MOLECULARLY IMPRINTED CARBON

(75) Inventors: Susan V. Olesik, Dublin, OH (US);
Joseph W. Zewe, Marion Center, PA (US)

(73) Assignee: THE OHIO STATE UNIVERSITY RESEARCH FOUNDATION, Columbus, OH (US)

( * ) Notice: Subject to any disclaimer, the term of this patent is extended or adjusted under 35 U.S.C. 154(b) by 1110 days.

(21) Appl. No.: 13/582,339

(22) PCT Filed: Mar. 2, 2011

(86) PCT No.: PCT/US2011/026809
§ 371 (c)(1),
(2), (4) Date: Jan. 10, 2013

(87) PCT Pub. No.: WO2011/109473
PCT Pub. Date: Sep. 9, 2011

(65) Prior Publication Data
US 2013/0116111 A1    May 9, 2013

Related U.S. Application Data

(60) Provisional application No. 61/309,681, filed on Mar. 2, 2010.

(51) Int. Cl.
B01J 20/32    (2006.01)
C01B 31/02    (2006.01)
(Continued)

(52) U.S. Cl.
CPC ............. B01J 20/324 (2013.01); B01J 20/20 (2013.01); B01J 20/205 (2013.01);
(Continued)

(58) Field of Classification Search
CPC ........ B01J 20/324; B01J 20/20; B01J 20/205; B01J 20/3057; B01J 20/3078; B32B 3/30;
(Continued)

(56) References Cited

U.S. PATENT DOCUMENTS 5,348,917 A    9/1994   Keller et al.
5,399,460 A *  3/1995   Aldrich ................. G03F 7/0387
                                                    430/281.1

(Continued)

FOREIGN PATENT DOCUMENTS

EP    1203953    5/2002
WO    98/42620   10/1998
(Continued)

OTHER PUBLICATIONS

Szumski, Michael and Boguslaw Buszewski. "Molecularly imprinted polymers: A new tool for separation of steroid isomers", Jul. 2004, Journal of Separation Science, vol. 27, Issue 10-11, p. 837-842.*

(Continued)

Primary Examiner — Maria Veronica Ewald
Assistant Examiner — Ethan Weydemeyer
(74) Attorney, Agent, or Firm — Michael Best & Friedrich LLP

(57) ABSTRACT

Preparation of a molecularly imprinted carbon is described. The molecularly imprinted carbon has a surface that is imprinted on the molecular level for a specific template molecule of interest, making it highly selective for analytes corresponding to at least a portion of the template molecule. Devices including the molecularly imprinted carbon and their use in methods of detecting analytes are also described. As an example, dibutyl butylphosphonate (DBBP), a surrogate for chemical warfare agents, was used as a template molecule. Electrospun molecularly imprinted SU-8 and (Continued)

pyrolyzed polymer (PP) solid-phase microextraction (SPME) devices were prepared; their ability to preferentially extract DBBP from an aqueous matrix, with and without interferences present, was evaluated via comparison with non-imprinted SU-8 and PP SPME fibers. The electrospun devices demonstrated a higher selectivity for DBBP, as evidenced by their extraction time profiles. The MI-SPME fibers tested extracted at least 60% more DBBP than their non-imprinted counterparts.

12 Claims, 10 Drawing Sheets

(51) Int. Cl.
  B01J 20/20      (2006.01)
  B32B 3/30       (2006.01)
  B01J 20/30      (2006.01)
  G01N 1/40       (2006.01)

(52) U.S. Cl.
  CPC ....... *B01J 20/3057* (2013.01); *B01J 20/3078* (2013.01); *B32B 3/30* (2013.01); *C01B 31/02* (2013.01); *G01N 1/405* (2013.01); *G01N 2600/00* (2013.01); *Y10T 428/24802* (2015.01)

(58) Field of Classification Search
  CPC .... C01B 31/02; G01N 1/405; G01N 2600/00; Y10T 428/24802
  USPC .......... 428/195.1, 408; 502/5, 406, 416, 437
  See application file for complete search history.

(56) References Cited

U.S. PATENT DOCUMENTS

| | | | |
|---|---|---|---|
| 6,808,746 B1 | 10/2004 | Dai et al. | |
| 6,811,957 B1 | 11/2004 | Mau et al. | |
| 6,921,670 B2 | 7/2005 | Carpenter | |
| 7,056,455 B2 | 6/2006 | Matyjaszewski et al. | |
| 2002/0053284 A1* | 5/2002 | Koros ................. | B01D 53/228 95/51 |
| 2004/0024076 A1 | 2/2004 | Davis | |
| 2008/0113283 A1 | 5/2008 | Ghoshal et al. | |
| 2008/0203380 A1 | 8/2008 | Wang et al. | |
| 2009/0169466 A1 | 7/2009 | Yamakawa et al. | |
| 2009/0264317 A1 | 10/2009 | Ofir et al. | |

FOREIGN PATENT DOCUMENTS

| | | |
|---|---|---|
| WO | 2010/030900 | 3/2010 |
| WO | 2011/109473 | 9/2011 |

OTHER PUBLICATIONS

Campbell et al, "Fabrication of photonic crystals for the visible spectrum by holographic lithography", Published Mar. 2, 2000, letters to nature, Macmillan Magazines Ltd, vol. 404, pp. 53-56.*
ChemicalBook, "3-Methacryloxypropyltrimethoxysilane", Dec. 2010, pp. 1-3.*
Szumski et al, "Molecularly Imprinted Polymers: A New Tool for Separation of Steroid Isomers", Published Jul. 7, 2004, Journal of Separation Science, John Wiley & Sons, Inc., vol. 27, pp. 837-842.*
Menendez-Diaz et al. "Types of carbon adsorbents and their production," Dec. 2006, Activated Carbon Surfaces in Environmental Remediation, Elsevier Ltd., pp. 1-47.*
Wired Chemist, "Common Bond Energies (D) and Bond Lengs (r)"—Adapted from Huheey, "The Strentgths of Chemical Bonds", 2nd ed., Butterworths, London, Dec. 1958 and Darwent, "National Standard Reference Data Series", National Bureau of Standards, No. 31, Washington, DC, Dec. 1970 and S.W. Beneson, J, Chem. Educ., 42, p. 502, Dec. 1965.*
Bagheri et al., Anal. Chim. Acta, 532, 89-95 (2005).
Chronakis et al., Macromolecules, 39, 357-361 (2006).
Clark et al., "Technique for Ultrathin Layer Chromatagraphy Using Electrospun,"Nanofibrous Stationary Phase, 2009, pp. 4121129.
Dai et al., "Functionalized surfaces based on polymers and carbon nanotubes for some biomedical and optoelectronic applications," 2003 Nanotechnology 14 1081.
Dietz et al., J. Chromatogr. A, 1103, 183-192 (2006).
Jiang et al., "Carbon nanotube-coated solid-phase microextraction metal fiber based on sol-gel technique," Journal of Chromatography a (Sep. 2009).
Jiang et al., Chromatogr. Sci. 44, 324-332 (2006).
Le Moullec et al., J. Chromatogr. A, 1139, 171-177 (2007).
Malosse et al., Analyst, 133, 588-595 (2008).
Musteata et al., J. Anal. Chem., 79, 6903-6911 (2007).
Pawliszyn, J., "Solid Phase Microextraction Theory and Practice," Chap. 2, 11-42 (1997).
Steach et al., J. Appl. Polym. Sci., 118 405-412 (2010).
Turiel et al., Anal. Chem., 79, 3099-3104 (2007).
Gawdzik et al., J. Liq. Chromatogr. Rel. Technol, 27, 1027-1041 (2004).
Wang et al., J. Chromatogr. A, 893, 157-168 (2000).
Yin et al., "Fabrication of carbon nanotube arrays for field emission and sensor devices by nanoimprint lithography," Microelectronics Journal, vol. 40, Issue 3, Mar. 2009, pp. 604-607.
Zewe et al., Anal. Chem. 82, 5341-8 (2010).
International Search Report and Written Opinion for Application No. PCT/US11/26809 dated Jun. 16, 2011 (6 pages).
Li et al., "Colloid-Imprinted Carbons as Stationary Phases for Reverse-Phase Liquid Chromatography," 2004, Anal. Chem, 76, 5479-5485.

* cited by examiner

MOLECULARLY IMPRINTED CARBON

CROSS REFERENCE TO RELATED APPLICATIONS

This application is a national stage filing under 35 U.S.C. 371 of International Patent Application No. PCT/US2011/026809, filed Mar. 2, 2011, which claims the benefit of U.S. Provisional Application No. 61/309,681, filed Mar. 2, 2010, the disclosures of which are hereby incorporated by reference as if recited herein in their entirety.

GOVERNMENT FUNDING

The present invention was supported by National Science Foundation (NSF) Grant Number NSF-0616709. The Government has certain rights in this invention.

BACKGROUND

Molecular imprinting is the process through which polymers with recognition properties tailored toward a specific template molecule are prepared. This is accomplished by cross-linking a synthetic polymer in the presence of a template molecule. The template molecule is subsequently removed from the resulting cross-linked polymer matrix by washing, leaving behind cavities within the polymer that are complementary in size, shape, and chemical functionality of the template within the polymer. The resulting molecularly imprinted polymers (MIPs) are able to selectively bind to the template molecules in the presence of other molecules. Le Moullec et al., J. Chromatogr. A, 1139, 171-177 (2007); Turiel et al., Anal. Chem., 79, 3099-3104 (2007). This ability makes them ideally suited to a variety of applications, including affinity-based separations, biomimetic sensors, and various organic syntheses. MIPs possess many advantages over established techniques, such as synthetic antibodies, in that they are more chemically and thermally stable, as well as less expensive to produce. Chronakis et al., Macromolecules, 39, 357-361 (2006) However, the molecular template in some MIPs has been shown to degrade with repeated use, decreasing the MIPs' selectivity for its template molecule over time.

Solid phase microextraction (SPME) is a solvent free extraction technique that has obtained widespread popularity in recent years due to it s ease of use, versatility, and robustness. Arthur et al., J. Anal. Chem., 62, 2145-2148 (1990). A SPME device consists of a small amount of an extractive material deposited onto a solid support, typically a fiber. The coated fiber is exposed to the sample of interest, where the analytes that are present are extracted via the extractive material coating. The analytes are then later desorbed from the extractive material coating into an analytical instrument, such as a gas chromatograph, for separation and quantitation. Pawliszyn, J. "Solid Phase Microextraction Theory and Practice", Chap. 2, 11-42 (1997).

SPME has been applied to a variety of applications, including the analysis of volatile and semi-volatile organic compounds in water samples as well as various in-vitro and in-vivo biological fluids. Musteata et al., J. Anal. Chem., 79, 6903-6911 (2007); Vawdzik et al., J. Liq. Chromatogr. Rel. Technol, 27, 1027-1041 (2004). The versatility of SPME is due primarily to the different types of fiber coatings that can be employed. There are no carbon SPME fibers currently commercially available. Dietz et al., J. Chromatogr. A, 1103, 183-192 (2006).

A number of different methods are described in the literature as having been utilized to fabricate SPME coatings, including sol-gel techniques (Wang et al., J. Chromatogr. A, 893, 157-168 (2000)) and electropolymerization. Bagheri et al., Anal. Chinn. Acta, 532, 89-95 (2005).The inventors recently developed a method to generate SPME fiber coatings via eletrospinning. Specifically, SU-8 2100, a negative photoresist, was electrospun onto stainless steel wires to give a coating comprised of a mat of nanofibers. However, there remains a need for imprinted coatings that exhibited higher selectivity or higher durability than those obtainable using these known techniques.

SUMMARY

The present invention provides improved coatings that can be molecularly imprinted. The inventors have demonstrated that electrospun nanofibers could be pyrolyzed in order to generate carbon nanofiber based SPME coatings. Zewe et al., Anal Chem. 82, 5341-8 (2010). This technique is expanded upon as described herein, where the generation of electrospun molecularly imprinted SU-8 (MI-SU-8) and carbon, or molecularly imprinted pyrolyzed polymer (MI-PP), nanofiber based SPME coatings is described. The molecularly imprinted carbon described herein has many advantages over molecularly imprinted polymers of the prior art. One of the primary advantages is that, due to the higher thermal stability of carbon relative to molecularly imprinted polymers, the molecularly imprinted carbon exhibits a longer operational lifetime. Molecularly imprinted-carbon should also be more chemically stable than conventional molecularly imprinted polymers.

Dibutyl butylphosphonate (DBBP) was utilized as the imprint molecule in the fabrication of MI-SU-8 and MI-PP SPME fibers. DBBP is a surrogate for various chemical warfare agents (CWAs), making it a template molecule of interest. Malosse et al., Analyst, 133, 588-595 (2008). The MI-SU-8 and MI-PP SPME fibers are evaluated herein by comparing their extraction performance versus non-imprinted SU-8 and PP fibers; specifically, their ability to preferentially extract DBBP from an aqueous matrix, with and without the presence of various interferences was compared. Additionally, the effect of electrospinning on the templating process was examined by comparing the extraction performances of silica slides coated with electrospun and spin-coated non-imprinted and MI-SU-8 and MI-PP in solid phase extraction (SPE) studies.

The present invention differs from earlier work in solid phase microextraction using molecularly imprinted coatings in that the substrate carrying the molecularly imprinted polymer (the "pyrolysis preform") is heated under conditions which causes the molecularly imprinted coating to pyrolyze into a carbonaceous coating retaining the pattern of molecular imprints in the coating before pyrolysis.

In one aspect, the present invention provides a pyrolyzed molecularly imprinted polymer. In one embodiment, the polymer is a polymer suitable for being pyrolyzed to form a nongraphitizable carbon selected from the group consisting of cellulose, poly(furfuryl alcohol) or a furfuryl alcohol copolymer, poly(vinylidene chloride), resorcinol-phenol copolymer, highly unsaturated polymers, polyimide, and polyacrylonitrile. In another embodiment, the polymer is a photoresist polymer, such as an epoxy-based negative photoresist polymer. In a further embodiment, the polymer is imprinted by a template molecule having a size of 1 micron or less.

Another aspect of the invention provides a device comprising a solid support, at least a portion of the surface of the solid support carrying a molecularly imprinted carbon layer thereon. In one embodiment, the molecularly imprinted carbon layer is formed from carbon nanofibers. In another embodiment, the device is a solid phase microextraction device. In a further embodiment, the molecular imprinted carbon layer comprises a plurality of cavities on the surface of the carbon layer having a shape corresponding to at least a portion of a template molecule having a size of 1 micron or less. In yet other embodiments, the molecular imprinted carbon layer has been imprinted using a plurality of different template molecules, or the device includes a plurality of regions that each have been molecularly imprinted by a different template molecule.

In further embodiments of the device of the invention, the molecularly imprinted carbon layer is produced by forming a polymer surface layer on the support by electrospinning, cross-linking the polymer surface layer in the presence of a template molecule, removing the template molecule to form a molecularly imprinted polymer surface layer and then pyrolyzing the molecularly imprinted polymer surface layer. Additional embodiment make use of apolymer is selected from the group consisting of cellulose, poly(furfuryl alcohol) or a furfuryl alcohol copolymer, poly(vinylidene chloride), resorcinol-phenol copolymer, highly unsaturated polymers, polyimide, and polyacrylonitrile, or an epoxy-based negative photoresist polymer.

Another aspect of the invention provides a process for selectively extracting an analyte from a sample comprising contacting the sample with the device of the invention in which the molecularly imprinted carbon layer thereof comprises a plurality of cavities on the surface of the carbon layer having a shape corresponding to at least a portion of the analyte. In one embodiment, the portion of the analyte corresponds to a portion of a template molecule having a size of 1 micron or less. In another embodiment, the sample contains a carrier and a measurable quantity of at least one other molecule in addition to the analyte.

A further aspect of the invention provides a method of making a solid phase microextraction device, including the steps of: applying a mixture including a cross-linkable base polymer and a template molecule to at least a portion of the surface of a solid support; crosslinking the base polymer to form a molecularly imprinted polymer layer; extracting the template molecule from the molecularly imprinted polymer layer, and pyrolyzing the molecularly imprinted polymer layer to form a molecularly imprinted carbon layer.

Embodiments of the method include a base polymer selected from the group consisting of cellulose, poly(furfuryl alcohol) or a furfuryl alcohol copolymer, poly(vinylidene chloride), resorcinol-phenol copolymer, highly unsaturated polymers, polyimide, and polyacrylonitrile. In another embodiment, the base polymer comprises an epoxy-based negative photoresist. In a further embodiment of the method, the mixture is applied to the solid support by electrospinning. In yet another embodiment, the base polymer is crosslinked by exposure to UV light. In a further embodiment, the pyrolysis is conducted at a temperature within the range from about 550° C. to about 650° C.

BRIEF DESCRIPTION OF THE FIGURES

The present invention may be more readily understood by reference to the following figures, wherein.

DETAILED DESCRIPTION

Figure 1:
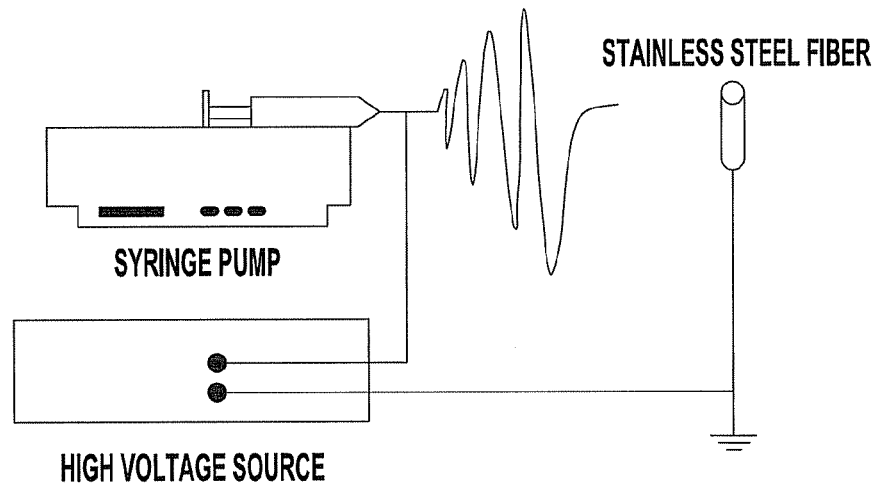
FIG. 1 provides a schematic representation of an electrospinning apparatus, depicting the preparation of electrospun-coated SPME fibers.

The following discussion is presented to enable a person skilled in the art to make and use the invention. Various modifications will be readily apparent to those skilled in the art, and the general principles disclosed herein may be applied to other embodiments and applications without departing from the scope of the present invention as defined by the appended claims. Thus, the present invention is not intended to be limited to the embodiments shown, but is to be accorded the widest scope consistent with the principles and features disclosed herein.

Definitions

Unless otherwise defined, all technical and scientific terms used herein have the same meaning as commonly understood by one of ordinary skill in the art to which this invention pertains. In case of conflict, the present specification, including definitions, will control.

The terminology as set forth herein is for description of the embodiments only and should not be construed as limiting of the invention as a whole. Unless otherwise specified, "a," "an," "the," and "at least one" are used interchangeably. Furthermore, as used in the description of the invention and the appended claims, the singular forms "a", "an", and "the" are inclusive of their plural forms, unless contraindicated by the context surrounding such.

Also herein, the recitations of numerical ranges by endpoints include all numbers subsumed within that range (e.g., 1 to 5 includes 1, 1.5, 2, 2.75, 3, 3.80, 4, 5, etc.).

In one aspect, the present invention provides a molecularly imprinted polymer that has been pyrolyzed to form a molecularly imprinted carbon-based structure. The molecularly imprinted polymer is a polymer that has been imprinted to include cavities corresponding to the shape of at least a portion of a template molecule. The template molecule can have a size of 1 micron or less, but the portion of the template molecule which actually forms the cavity can be substantially less. The molecularly imprinted polymer, also referred to herein as a pyrolysis "preform," can be prepared using the methods described herein.

The polymer is imprinted by including a template molecule in a base polymer mixture. The base polymer mixture is cross-linked to form a more permanent structure which retains the template molecules in cavities within the cross-linked polymer that surround at least a portion of the template molecules. The template molecules are then removed, resulting in a polymer that has been imprinted with the shape of at least a portion of the template molecules. The molecularly imprinted polymer has the capacity to bind the template molecules or analytes representing a portion thereof upon re-exposure as a result of the affinity of these template molecules for the cavities within the molecularly imprinted polymer resulting from the correspondence between the shape of the cavity and at least a portion of the template molecule. When presented with a variety of molecules in a sample, the cavities show a highly preferential binding to the analytes corresponding to the template molecule.

The molecularly imprinted polymer is then pyrolyzed to form a molecularly imprinted carbon-based structure. Pyrolysis represents a controlled burn of the polymer to replace the polymer with a carbon structure. The essential physical structure of the surface is retained during pyrolysis, but the chemical composition of the structure is changed. Accordingly, polymer fiber will be converted to carbon fiber, and cavities formed around template molecules will be retained in the molecularly imprinted carbon formed from the molecularly imprinted polymer as a result of pyrolysis. It will be appreciated that that this invention can be practiced on any coating formed from a molecularly imprinted polymer that is capable of pyrolyzing into a carbonaceous coating retaining the pattern of molecular imprints in the coating before pyrolysis. When the pyrolysis preform is applied to a substrate, it is preferably that the substrate retain its physical integrity when subjected to the pyrolysis reaction as well.

The polymer used as the pyrolysis preform should be a polymer suitable for being pyrolyzed to form a nongraphitizable carbon. Nongraphitizable carbon is carbon that will not result in the formation of crystalline graphite regardless of how much heat is applied to the polymer when it is pyrolyzed. Nongraphitizable carbon is a disordered carbon systems that includes nanosized graphitic sp2 carbon domains.

For the preparation of molecularly imprinted carbon, molecularly imprinted polymers having a high molecular carbon content are preferably used. That is to say, the amount of carbon atoms forming the polymer molecules which make up this polymer coating should be at least 50% of these polymer molecules on a weight basis. Polymers in which the amount of carbon atoms form at least 60 wt. %, at least 70 wt %, at least 75 wt. % or even at least 80 wt. % of these polymer molecules are preferred. Specific examples include not only various epoxy resins as described in the above working examples and also by polyacetylenes and various oligyne polymers, for example. For example, the polymer used can be selected from the group consisting of cellulose, poly(furfuryl alcohol) or a furfuryl alcohol copolymer, poly(vinylidene chloride), resorcinol-phenol copolymer, highly unsaturated polymers, polyimide, and polyacrylonitrile polymers.

For some applications, it may also be preferable that the polymer used is a photoresist polymer. Photoresist is a light-sensitive material used in various industrial processes, such as photolithography and photoengraving to form a patterned coating on a surface. Preferably, the polymer is a negative photoresist. Negative photoresists are a type of photoresist in which the portion of the photoresist that is exposed to light becomes insoluble to the photoresist developer. The unexposed portion of the photoresist is dissolved by the photoresist developer, allowing some portions of the substrate surface to remain uncovered. A preferred polymer is an epoxy-based negative photoresist, in particular the SU-8 series of negative photoresists.

The pyrolyzed molecularly imprinted polymer can also be provided as carbon fibers. In order to form carbon fibers, the pyrolysis preform should have a fiber structure that is retained during pyrolysis. The carbon fibers can be microfibers or nanofibers. Nanofibers have a diameter of less than 1 micron. Embodiments including nanofibers can have a fiber diameter from 50 to 800 nanometers, from 200 to 600 nanometers, or from 300 to 500 nanometers. The mass and diameter of the nanofibers generally decrease as the polymer is pyrolyzed to carbon, with increasing amounts of shrinkage as the temperature increases. For example, a mat of SU-8 polymer having a weight of 0.52 mg is converted to 0.33 mg of carbon by pyrolysis at 600° C., and to 0.20 mg of carbon by pyrolysis at 800° C. While pyrolysis does affect the size of the carbon fiber, it has surprisingly shown little effect on affinity of the molecularly imprinted carbon for the template molecules used to imprint the pyrolysis preform. The use of carbon fiber has the advantage of providing a coating with a greater surface area, which can provide for a greater amount of binding by template molecules. Pyrolysis of the pyrolysis preform also increases the surface area of the fibers.

Another aspect of the invention provides a device including a solid support, in which at least a portion of the surface of the solid support carries a molecularly imprinted carbon layer. Any significant amount of the surface of the solid support can include the carbon layer, and the carbon layer need not be contiguous. For example, the carbon layer can occupy from 5% to 100% of the surface of the solid support. The coating may exist directly on the surface of the solid support, or in some embodiments an additional adhesion material may be included between the carbon layer and the solid support to improve binding. In terms of solid supports, any material which will retain its structural integrity as a result of the pyrolysis reaction can be used as a support for the molecularly imprinted carbon layer. While the support need be solid in order to initially support the molecularly imprinted polymer and eventually the molecularly imprinted carbon later, the support need not be rigid. For example, in some embodiments it may be preferable to use flexible materials for the solid support. Metals, especially stainless steels and other metals that are un-reactive at the elevated temperatures and reducing conditions encountered during pyrolysis can be used, including Inconel and the like. Stainless steel is preferred due to availability, cost, and durability. Accordingly, in a preferred embodiment the solid support comprises stainless steel wires.

The carbon layer can vary in thickness, depending on the thickness of the pyrolysis preform that is applied to the surface of the solid support. For example, various embodiments of the molecularly imprinted carbon layer having a thickness from 2 to 50 micrometers, from 3 to 30 micrometers, or from 5 to 15 micrometers. The carbon layer will have the form of a mat when the carbon layer is made up of carbon fibers.

In a preferred embodiment, the device is a solid phase microextraction device. Solid phase microextraction (SPME) is a solvent-free extraction method. In order to function, the device merely needs to be able to carry a substantial amount of the molecularly imprinted material, and can thus vary substantially in shape. For convenience, rods of coated material are typically used. In some embodiments, the device can include portions that have been imprinted to be sensitive to various different molecular templates, such that the device can function as an array. Alternately, the carbon layer can have been molecularly imprinted with a variety of different molecular templates so that the device will extract a plurality of different analytes.

From the foregoing, it can be seen that a focus of this invention is on making molecularly imprinted carbon coatings for solid phase microextraction. However, this invention can also be used for making products which are useful in other applications. For example, products having molecularly imprinted carbonaceous surfaces made in accordance with this invention can be used for large scale bulk extractions, for making chromatographic stationary phases or supports, for making sensors for various different types of molecules and for other such utilities. Moreover, such products can be can be made in essentially any form such as, for example, in the form of a coated product as described above, in bulk (i.e., in the form of a mass of carbonaceous material not coated on or carried by a substrate) or any other desired physical form. If so, the molecularly imprinted surface of the product can be made from the same materials and according to the same pyrolysis approach as described above.

As described herein, the molecular imprinting present within the carbon layer comprises a plurality of cavities on the surface of the layer having a shape corresponding to at least a portion of a template molecule. As used herein a template "molecule" may in fact be a particle including a plurality of molecules, such as a virus particle. However, it is preferable that the template molecule have a size of 1 micron or less. In alternate embodiments, the template molecule may have a size of 500 nanometers or less, 250 nanometers or less, or 100 nanometers or less. In some embodiments nearly 100% of the template molecule may be used to form a cavity, while in other embodiments only a portion of the template molecule can be used to form a cavity. However, a single template molecule can have a plurality of regions that are useful for forming cavities as part of the molecular imprinting process.

In order for the template molecules to be removed, and for the resulting cavities to function to later extract the template molecules, the cavities must be present on the surface of the carbon layer, rather than be buried within its interior. Accordingly, it is preferable for the carbon layer to have a high surface area, as is the case when carbon fiber is used. By being present on the surface, it is meant that the cavity is accessible from outside the carbon fiber through a hole that forms part of the cavity and is positioned on the surface of the carbon layer.

As will be described in greater detail herein, the molecularly imprinted carbon layer is produced by forming a polymer surface layer on the support, cross-linking the polymer surface layer in the presence of a template molecule, removing the template molecule to form a molecularly imprinted polymer surface layer and then pyrolyzing the molecularly imprinted polymer surface layer to form a molecularly imprinted carbon layer.

Another aspect of the invention provides a method of making a solid phase microextraction device. The method includes the steps of applying a mixture including a cross-linkable base polymer and a template molecule to at least a portion of the surface of a solid support; crosslinking the base polymer to form a molecularly imprinted polymer layer; extracting the template molecule from the molecularly imprinted polymer layer, and pyrolyzing the molecularly imprinted polymer layer to form a molecularly imprinted carbon layer, resulting in the formation of a solid phase microextraction device that comprises a solid support, at least a portion of which carries a molecularly imprinted carbon layer.

Producing the molecularly imprinted polymer (i.e., the pyrolysis preform) in accordance with this aspect of the invention is done using known techniques, as described herein. That is to say, the pyrolysis preform is made in the same way that molecularly imprinted coatings have been made in the past, care being taken to select as the coating a high carbon content polymer as described above and a substrate which will retain its physical integrity as a result of the pyrolysis reaction. The molecularly imprinted polymer can be applied to the surface of the device using a variety of different methods known to those skilled in the art. See Dietz et al., J. Chromatogr. A, 1103, 183-192 (2006) and Jiang et al., J. Chromatogr. Sci. 44, 324-332 (2006). Examples of methods that can be used include the use of electrospinning, spin coating, sol-gel technology and electropolymerization.

The pyrolysis preform is prepared from a cross-linkable base polymer. The cross-linkable polymer includes monomers which cross-link to form a solid structure, as is known to those skilled in the art. Cross-linking can be induced, for example, either chemically or by irradiation. A cross-linking agent can also be provided to the mixture to facilitate cross-linking. In the case of SU-8 polymer, a cross-linking agent is used and the base polymer is crosslinked by exposure to UV light.

The cross-linkable base polymer and the template molecule are applied to the solid support as a mixture. A solvent capable of supporting both the base polymer and the template molecules is used to provide the mixture. For example, for SU-8 and various phenyl compounds, cyclopentanone provides a suitable solvent. The use of 2-10% template molecule and 70-80% SU-8 polymer as the range with 2% and 75% SU-8 are a preferred composition for the mixture.

A preferred method of applying the mixture to the solid support is by electrospinning. Electrospinning of polymeric fibers provides the capability to create micro or nanosized fibers. Electrospinning involves placing a high electric field between a polymer solution and a conductive collector. When the electric field is strong enough to overcome the surface tension of the droplet, a Taylor cone is formed. Following the creation of the Taylor cone, polymeric nanofibers are ejected toward the conductive collector. See Ramakrishna et al., "An introduction to Electrospinning and Nanofibers," World Scientific, Rivers Edge N.J. (2005). A detailed description of the use of electrospinning is provided within the Example provided herein. Parameters for the optimization of electrospinning of the photoresist polymer SU-8 are described by Steach et al., J. Appl. Polym. Sci., 118 405-412 (2010).

Once the pyrolysis preform is made, it is pyrolyzed to produce a carbonaceous coating retaining the pattern of molecular imprints in the coating that were present before pyrolysis. This can be accomplished by heating the pyrolysis preform in an inert or a moderately reducing atmosphere at elevated temperatures ranging from 400° C. to 800° C. for a suitable period of time, e.g., at least 5 hours or so, to cause destructive distillation of the of the material forming the molecularly imprinted coating. Pyrolysis temperatures as low as 300° C. and as high as 1500° C. are contemplated, depending on the nature of the atmosphere used for the pyrolysis reaction as well as the time of the pyrolysis reaction. Similarly, pyrolysis times as short as 1 hour or so and as long as 5 days or so are contemplated, again depending on the nature of the atmosphere used for the pyrolysis reaction as well as the temperature of the pyrolysis reaction. As indicated by the data provided in the Example herein, pyrolysis conducted at a temperature within the range from about 550° C. to about 650° C. appears to provide the best results.

In this regard, inert atmospheres can be used for the pyrolysis reaction, although a moderately reducing atmosphere is preferred in order to capture any fugitive oxygen or other reactive chemical that might be present, either as a result of decomposition of the material forming the molecularly imprinted polymer coating, outgassing of fugitive ingredients from the substrate of the pyrolysis preform, or both. As illustrated in the working examples, a moderately reducing atmosphere composed predominantly of an inert gas and containing a minor amount, e.g., about 1-40 vol. %, more typically 2-20 vol. %, 3-15 vol. %, 4-10 vol. %, or even about 5 vol. % $H_2$ or other mildly reducing gas is preferred. Oxidizing gases should not used so as to avoid degrading the molecularly imprinted carbon.

Another aspect of the invention provides a process for selectively extracting an analyte from a sample using a device a including a solid support in which at least a portion of the surface of the solid support carries a molecularly imprinted carbon layer. The process includes contacting the sample with a device including a solid support carrying molecularly imprinted carbon layer that includes a plurality of cavities on the surface of the carbon layer having a shape corresponding to at least a portion of the analyte.

The process can further include the step of detecting the extraction of an analyte from a sample. For example, a change in the physical characteristics of the carbon layer upon extraction of the analyte into the cavities on the surface of the carbon layer can be detected. Alternately, the presence of the analyte on the carbon layer can be detected directly, for example through spectroscopic methods. Extraction can be detected by demonstrating a decrease in the level of analyte in the sample. Alternately, the analytes can be desorbed from the molecularly imprinted carbon into an analytical instrument, such as a gas chromatograph, for separation and quantitation.

The term analyte, as used herein, refers to a molecule that corresponds to at least a portion of the template molecule. In some embodiments, the analyte and the template molecule can be the same. For example, the analyte and template molecule (DBBP) in the Example described herein are the same. However, the analyte can also represent a portion of the full template molecule. A template molecule can therefore provide a device of the invention with sensitivity to a plurality of analytes in some embodiments. For example, a virus particle can be used as a template molecule, but only the protein coat of the virus can be used as an analyte. Alternately, the template molecule can include additional material such as a solubility-enhancing portion to increase the solubility of the template in the mixture, but irrelevant as an analyte of interest.

The process for extracting an analyte using the device of the invention can be used for a variety of different analytes of interest. Essentially any analyte corresponding to at least a portion of a suitable template molecule can be used. One class of analytes of interest are chemical warfare agents of which dibutyl butylphosphonate (DBBP) acts as a surrogate. The device of the invention used in a process for detecting chemical warfare agents could provide a useful, solvent-free method for detecting exposure to harmful agents in an environment where exposure to chemical warfare agents is deemed likely. A particular example of analytes that can be readily extracted are phosphorus containing analytes such as phosphorus containing chemical warfare agents, which exhibit a high affinity for molecularly imprinted carbon. Alternately, the process for extracting an analyte using the device of the invention can be used to monitor for hazardous chemicals in the workplace, or a wide variety of other applications where the detection of a chemical in the environment is desirable.

A large variety of samples useful as a source for analyte are contemplated herein. A sample can be a conventional sample, such as a portion of a fluid such as wastewater or a bodily fluid. Alternately, the term sample can be used in the broader sense to encompass mere exposure of the device to an environment. For example, in the example of use of the process to detect chemical warfare agents, the sample can simply be the air through which a user bearing the device passes over a discrete period of time. The process of the present invention can be used on any of the samples suitable for being studied by conventional SPME; see Musteata et al., J. Anal. Chem., 79, 6903-6911 (2007) and Vawdzik et al., J. Liq. Chromatogr. Rel. Technol, 27, 1027-1041 (2004). In some simple embodiments, the sample merely contains a carrier which suspends the analyte (e.g., water or air) and a single analyte. However, more complex embodiments in which the sample contains a carrier and a measurable quantity of at least one other molecule in addition to the analyte are also contemplated. In addition, as noted herein, the device of the present invention can be configured to detect multiple analytes, either separately or as a class.

The following example is provided for illustrative purposes only and is in no way intended to limit the scope of the present invention.

EXAMPLE

In this example, the inventors demonstrate that electrospun molecularly imprinted (MI)-SU-8 and molecularly imprinted pyrolyzed polymer (MI-PP) SPME devices have a higher selectivity for DBBP, as illustrated by their extraction time profiles. All MI-SPME fibers extracted at least 60% more DBBP than their non-imprinted counterparts. The MI-600° C. fibers showed the largest effect, extracting more than five times the amount of DBBP relative to the non-imprinted 600° C. SPME fiber. Additionally, several solid phase extraction (SPE) studies were performed to determine the effect of electrospinning on the templating process, by comparing the extraction performance of both electrospun and spin-coated MI-SU-8 and MI-PP silica chips.

Experimental

Materials

Dibutyl butylphosphonate (90%), dioctyl phenylphosphonate (95%), benzene (99.9%), toluene (99.8%)), ethylbenzene (99.8%)), and o-xylene (98%)) were utilized in the extractions and were purchased from Sigma Aldrich. HPLC grade methanol was used in the preparation of the DBBP and DOPP solutions; the benzene, toluene, ethylbenzene, and o-xylene solutions were prepared with dicholoromethane.

Equipment and Instrumentation

All compounds that were extracted via the SPME fibers were analyzed using a Hewlett- Packard 5890 Series II Plus gas chromatograph with a pressure controlled split/splitless injector port and flame ionization detector. An injection sleeve with an inner diameter of 0.75 mm was utilized, coupled with a HP-5MS GC capillary (0.25 μm film thickness, 30 m length, 0.255 mm inner diameter) from Agilent Technologies. A Spellman CZE 1000R high voltage power supply and a Harvard Model 33 dual syringe pump were both used in the electrospinning apparatus, illustrated in FIG. 1. A Lindberg/Blue TF55030A was used to pyrolyze the non-imprinted and MI- SU-8 coated SPME fibers to convert them to carbon.

Material Preparation for SPME Fiber Fabrication

The electrospinning solution for the non-molecularly imprinted SPME devices was a 75% (v/v) solution of SU-8 2100 negative photoresist (from MicroChem Corporation, Newton, Mass.) and cyclopentanone (from Sigma Aldrich). SU-8 2100 is comprised of an epoxy-type base polymer and a photoreactive crosslinking agent. The resist hardens when it is exposed to UV light, as the cross-linking agent cross-links the polymer. For this reason, all treatment of the SU-8 solution was performed under yellow light to ensure the SU-8 was not prematurely crosslinked. This solution was stirred for a minimum of 24 hours to ensure homogeneity before it was drawn into a 10 mL syringe for electrospinning. Care was taken to ensure that the solution within the syringe was free of air bubbles prior to electrospinning.

The electrospinning solution for the MI-SPME devices was identical to the aforementioned solution, save for the addition of DBBP to the solution. The final concentration of DBBP in the electrospinning solution was 0.1 M. Following the addition of the DBBP, the solution was stirred for at least 48 hours before being transferred to a 10 mL syringe for electrospinning; this extended stirring time served to allow for association between the SU-8 and the DBBP template molecule. The collector utilized in all of these electrospinning trials, were small stainless steel fibers, with a diameter of ~127 μm, from Small Parts (Miami Lakes, Fla.). These stainless steel fibers were cut to an overall length of 1.5 cm, cleaned with methanol, and dried in an oven for 30 minutes at 80° C. prior to electrospinning.

SPME Fiber Fabrication.

The electrospinning parameters used here are described by Zewe et al., Anal Chem. 82, 5341-8 (2010). The stainless steel fibers were located 10 cm from the end of the syringe holding the electrospinning solution, connected to the ground by an alligator clip. The applied voltage was 9 kV and the flow rate or the electrospinning solution was 0.02 mL/min. The duration of electrospinning for all fibers was one minute. Once the stainless steel wires were coated with the electrospun SU-8 fibers, they were exposed to UV light for five minutes to crosslink the SU-8 fibers.

Preparation of Molecularly Imprinted SU-8 Fibers

Figure 2:
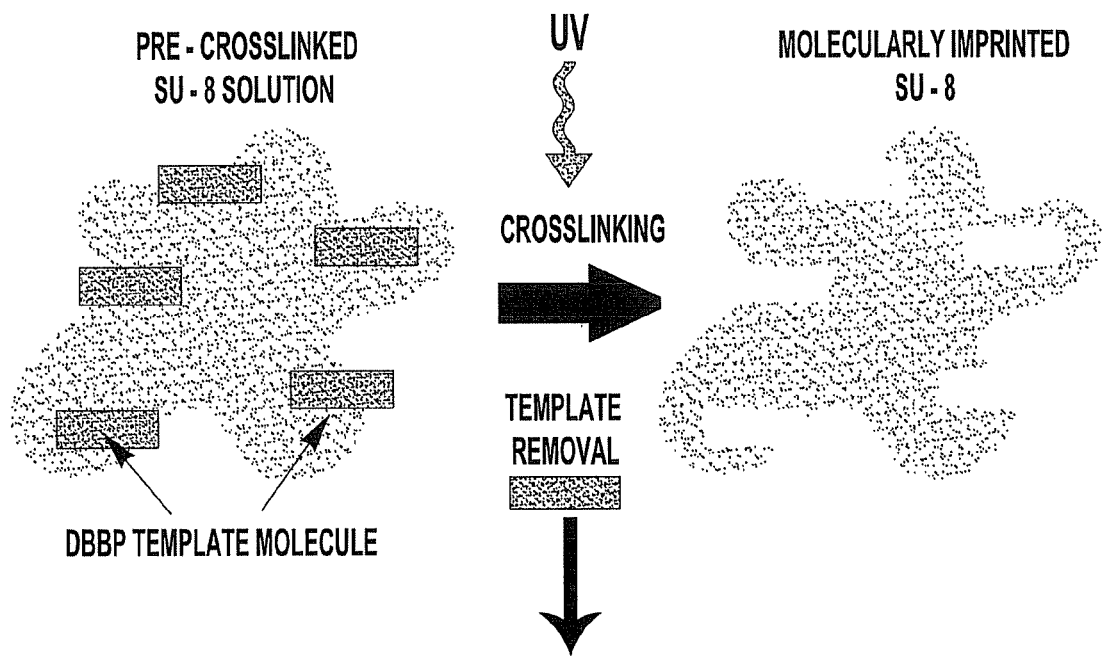
FIG. 2 provides a schematic representation of the preparation of molecularly imprinted-SU-8 with DBBP template molecule. DBBP is mixed into the SU-8 electrospinning solution, where the DBBP and SU-8 molecules are in dynamic equilibrium. The solution is then electrospun onto the stainless steel wires and cross-linked, hardening the SU-8 polymer matrix. The DBBP template molecule is then removed from the hardened polymer matrix via washing and exhaustive Soxhlet extraction, giving molecularly imprinted-SU-8 specific for DBBP.

Once the stainless steel fibers coated with the DBBP/SU-8 electrospun fibers were crosslinked by exposure to UV light, they were placed in a vial of heptane for at least 24 hours. The solution inside the vial was magnetically stirred during this time. After, the fibers were subjected to exhaustive Soxhlet extraction for a minimum of 24 hours, also using heptane. The purpose of these steps was to remove the DBBP template molecules from the polymer matrix, leaving behind MI-SU-8 nanofibers. A graphical representation of the mechanism of the molecular imprinting process is shown in FIG. 2.

Pyrolysis of Electrospun SU-8 Fibers

In order to generate carbon-coated SPME devices, wires covered with electrospun SU-8 nanofibers were pyrolyzed in a Lindberg/Blue TF55030A quartz tube furnace. The electrospun-coated wires were placed inside the quartz tube, and a forming gas mixture (95% $N_2$ and 5% $H_2$) was flowed continuously through the tube for the duration of the pyrolysis; forming gas was initially flowed through the tube for 20 minutes before the pyrolysis was started to ensure that all oxygen had been purged from the tube. A ramp rate of 1° C./min was used until the desired final pyrolysis temperature was reached; the fibers were held at the final temperature for a minimum of 5 hours before they were allowed to cool to room temperature. Fibers that had been pyrolyzed to 400, 600, 700, and 800° C. were utilized in this study.

Pyrolysis conditions for molecularly-imprinted and non-imprinted fibers were identical; however, prior to pyrolysis, the template molecule (DBBP) was removed from the fibers via washing and Soxhlet extraction, as described above.

SPME Fiber Assembly

Commercial SPME fiber assemblies were retrofitted with the electrospun coated stainless steel fibers; the coated fibers were attached to the assemblies with a high-temperature epoxy (from Epoxy Technology, Billerica, Mass.) that was cured in an oven for one hour at a temperature of 80° C. Once the epoxy was cured, the fibers were placed in the GC inlet for at least 30 minutes and held there until a steady signal baseline was achieved. The temperature of the inlet was 300° C.

Coating and Treatment of Silicon Chips for SPE

Chips of silicon wafers that were cut into 1.0×1.5 cm squares for the extraction experiments. These chips were subsequently washed with methanol and then dried in an oven at 80° C. for 30 minutes. The electrospun-coated silicon chips were prepared in the same manner described for coating the SPME wires. The electrospinning time was 20 minutes.

A spin coating procedure was also used to coat the silicon chips. The spin coating parameters used for SU-8 2100, are available on the MicroChem Corp. website under information for the SU-8 photoresist product line. A WS-400A-6NPP/Lite single wafer spin processor (Lauren Technologies Corporation, North Wales, Pa.) was used to spin coat the silicon chips. The spin coating program consisted of an initial 5 second ramp, at a ramp rate of 100 rpm/s, to 500 rpm, which was held for 10 s. A second ramp, with a ramp rate of 300 rpm/s, was conducted for 8.3 seconds to reach a rotational speed of 3000 rpm; this was held for 30 s until the procedure was completed. 1 mL of either non-imprinted or MI-SU-8 was delivered at the beginning of the program. Cross-linking, template removal, and pyrolysis procedures for the spin-coated silicon chips were identical to those employed for the electrospun-coated silicon chips and the electrospun-coated SPME wires.

Extraction and Analysis Procedures

All extractions occurred in 40 mL EPA vials. The vials were capped with EPA PTFE/silicone (10/90) septa (from National Scientific, Rockwood, Tenn.). Nanopure water (18 MO -cm) was utilized in all extractions; all analytes were present at a concentration of 40 ppm. All solutions were stirred using a Teflon stir bar (Fisher Scientific, Hanover Park, Ill.), controlled by an IKA C-MAG HS7 stir plate at a power level of 50%. Extraction time profiles were comprised by extracting DBBP, as well as DBBP and a BTEX mixture. Nanopure water within the vial was spiked with each of the test compounds, and allowed to stir for 20 minutes before the SPME fiber was introduced to the system. The fiber remained within the system for its allotted time period, after which it was transferred to the gas chromatograph.

Results and Discussion

Comparison of Molecularly Imprinted and Non-imprinted Electrospun SPME Fibers

Figure 3:
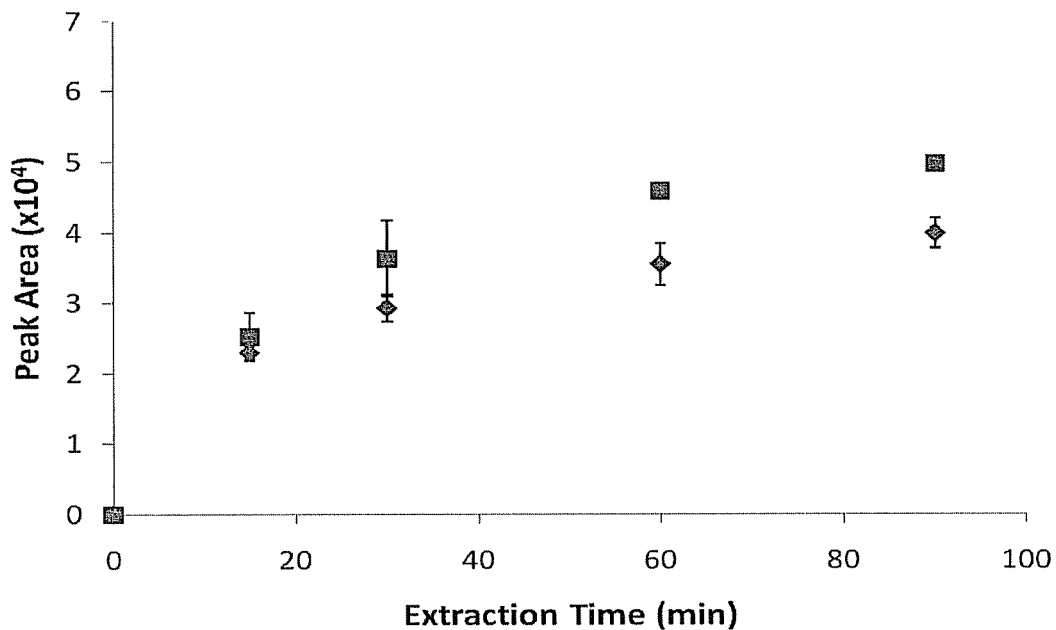
FIG. 3 provides a graph showing the extraction efficiency versus time profiles for the direct extraction of 40 ppm DBBP with an electrospun MI-SU-8 SPME fiber (♦) and an electrospun non-imprinted SU-8 SPME fiber (■). Constant stirring at room temperature, stirring speed set to 50% of maximum. GC conditions: 30° C. for 1 min, then programmed at 5° C./min to 100° C., 12° C./min to 140° C., and 2° C./min to 190° C.; inlet temperature set at 300° C. and detector temperature set at 300° C.

The superior selectivity for DBBP of the electrospun MI-DBBP SU-8 SPME fibers with respect to electrospun non-imprinted SU-8 SPME fibers was initially demonstrated by comparing the extraction time profiles for each fiber for the direct extraction of 40 ppm DBBP from an aqueous matrix. The results of these extractions are shown in FIG. 3.

Once equilibrium is reached at approximately 60 minutes, the MI-SU-8 SPME fibers extracted significantly more DBBP than the non-imprinted SU-8 SPME fibers. Since the amount, as measured by weight, of electrospun phase (SU-8) was present on both fibers, these results suggest that the MI-SU-8 fibers had a larger distribution constant with respect to DBBP than the non-imprinted fibers. This trend was also observed when both types of fibers were applied to a more complex matrix that also contained 40 ppm of benzene (B), toluene (T), ethylbenzene (E), and o-xylene (X), commonly referred to as BTEX as a group of compounds.

Figure 4A:
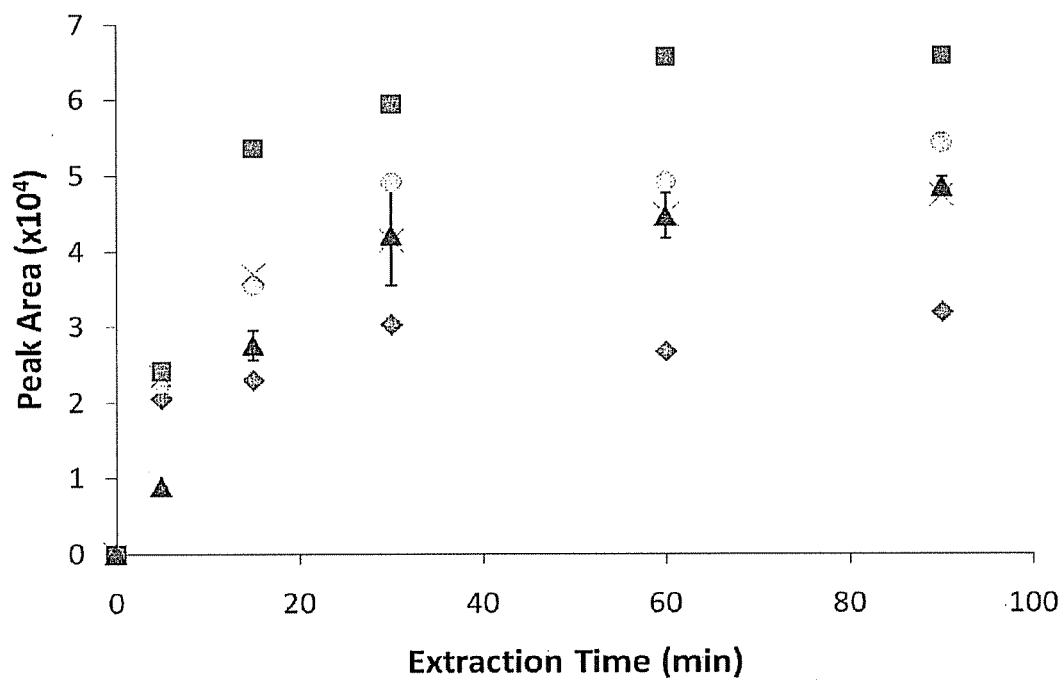
FIG. 4A provides a graph showing the extraction efficiency versus time profiles for the direct extraction of 40 ppm each of DBBP (▲), benzene (♦), toluene (●), ethylbenzene (■), and o-xylene (X) with an electrospun MI-SU-8 SPME fiber. Constant stirring at room temperature, stirring speed set to 50% of maximum. GC conditions: 30° C. for 1 min, then programmed at 5° C./min to 100° C., 12° C./min to 140° C., and 2° C./min to 190° C.; inlet temperature set at 300° C. and detector temperature set at 300° C.
Figure 4B:
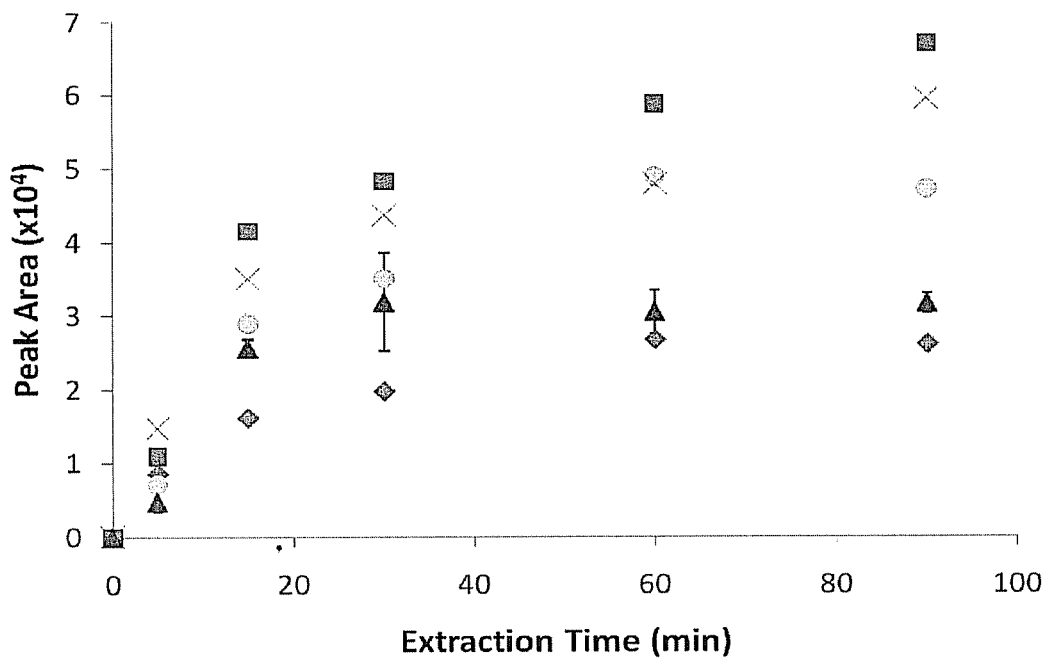
FIG. 4B provides a graph showing the extraction efficiency versus time profiles for the direct extraction of 40 ppm DBBP (▲) in an aqueous matrix containing 40 ppm of benzene (♦), toluene (●), ethylbenzene (■), and o-xylene (X) with an electrospun non-imprinted SU-8 SPME fiber. Constant stirring at room temperature, stirring speed set to 50% of maximum. GC conditions: 30° C. for 1 min, then programmed at 5° C./min to 100° C., 12° C./min to 140° C., and 2° C./min to 190° C.; inlet temperature set at 300° C. and detector temperature set at 300° C.
Figure 4C:
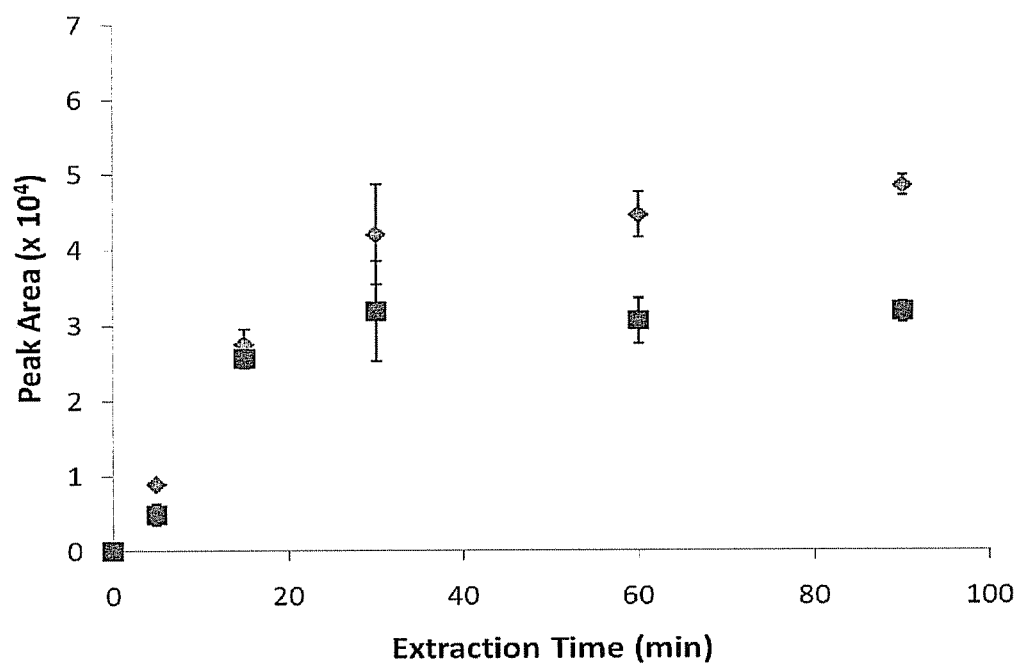
FIG. 4C provides a graph comparing the amount of DBBP extracted by the electrospun MI-SU-8 SPME fiber (♦) and the electrospun non-imprinted SU-8 SPME fiber (■) from an aqueous matrix containing 40 ppm of DBBP and BTEX. Constant stirring at room temperature, stirring speed set to 50% of maximum. GC conditions: 30° C. for 1 min, then programmed at 5° C./min to 100° C., 12° C./min to 140° C., and 2° C./min to 190° C.; inlet temperature set at 300° C. and detector temperature set at 300° C.

The results of these experiments are presented in FIG. 4. The results in FIG. 4 illustrate that the competition between BTEX and DBBP for the adsorption sites on SU-8 deceases the equilibrium time (30 minutes for competitive extraction, 60 minutes for extraction of DBBP without BTEX compounds). Furthermore when the relative extraction of the BTEX compounds is compared, the presence of the molecular imprint seems to impact the amount of o-xylene extracted in that the extraction of o-xylene is decreased for the imprinted fiber.

Figure 5:
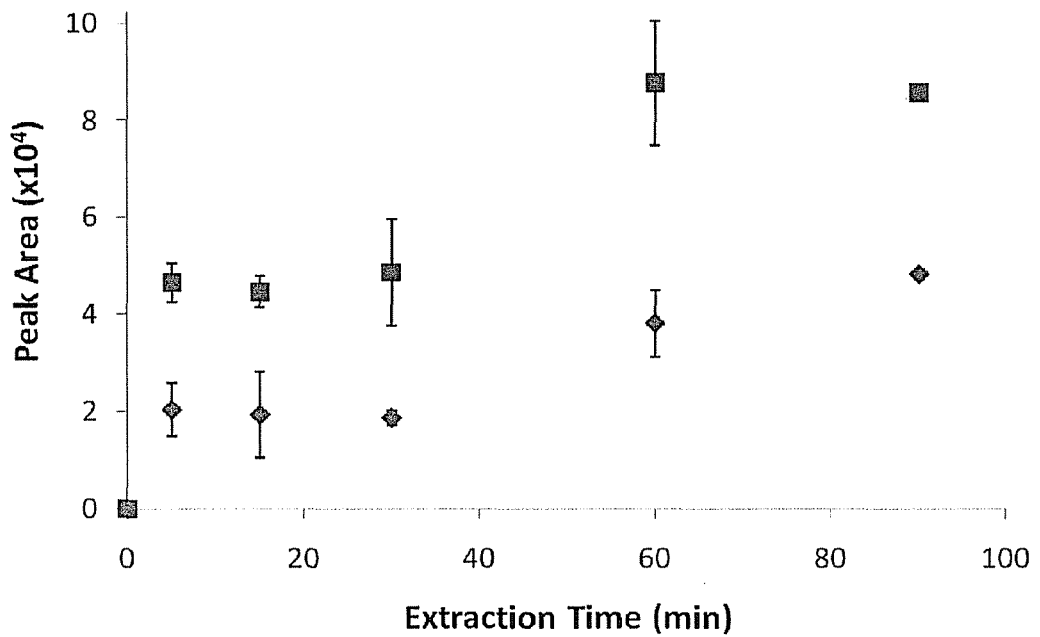
FIG. 5 provides a graph showing the extraction efficiency versus time profiles for the direct extraction of 40 ppm DBBP with an electrospun MI-400° C. SPME fiber (■) and an electrospun non-imprinted 400° C. SPME fiber (♦). Constant stirring at room temperature, stirring speed set to 50% of maximum. GC conditions: 30° C. for 1 min, then programmed at 5° C./min to 100° C., 12° C./min to 140° C., and 2° C./min to 190° C.; inlet temperature set at 300° C. and detector temperature set at 300° C.
Figure 6:
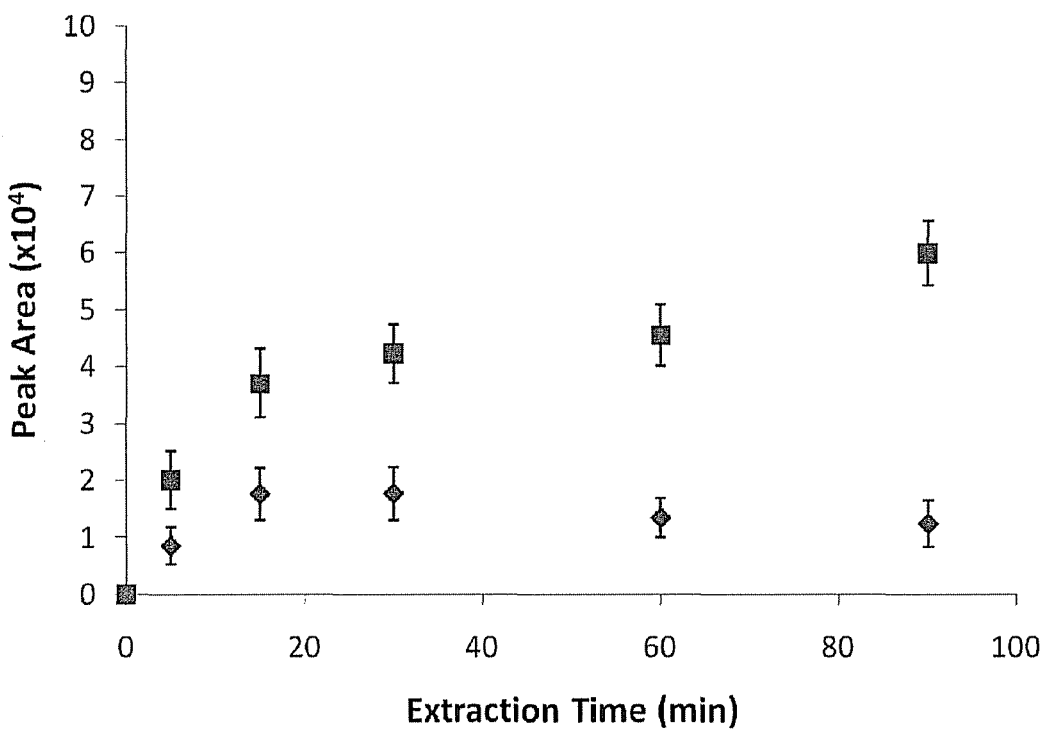
FIG. 6 provides a graph showing the extraction efficiency versus time profiles for the direct extraction of 40 ppm DBBP with an electrospun MI-600° C. SPME fiber (■) and an electrospun non-imprinted 600° C. SPME fiber (♦). Constant stirring at room temperature, stirring speed set to 50% of maximum. GC conditions: 30° C. for 1 min, then programmed at 5° C./min to 100° C., 12° C./min to 140° C., and 2° C./min to 190° C.; inlet temperature set at 300° C. and detector temperature set at 300° C.
Figure 7:
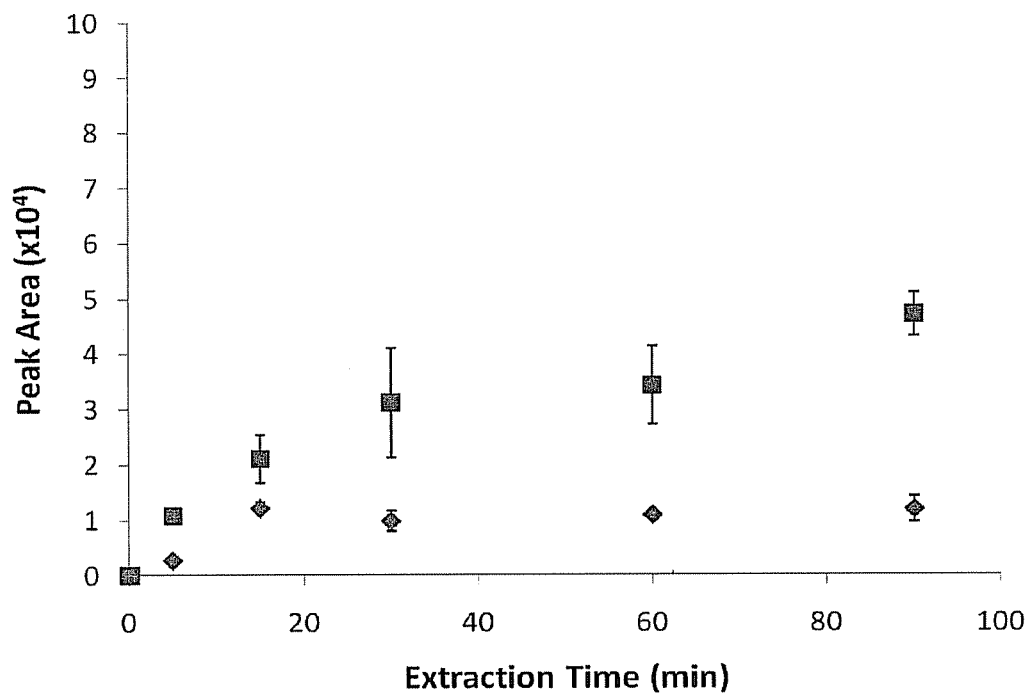
FIG. 7 provides a graph showing the extraction efficiency versus time profiles for the direct extraction of 40 ppm DBBP with an electrospun MI-800° C. SPME fiber (■) and an electrospun non-imprinted 800° C. SPME fiber (♦). Constant stirring at room temperature, stirring speed set to 50% of maximum. GC conditions: 30° C. for 1 min, then programmed at 5° C./min to 100° C., 12° C./min to 140° C., and 2° C./min to 190° C.; inlet temperature set at 300° C. and detector temperature set at 300° C.

The performance of the MI-PP fiber-coated wires was also compared to that of the non-imprinted PP electrospun fiber-coated SPME fibers. Molecularly-imprinted and non-imprinted fibers pyrolyzed at 400, 600, and 800° C. were first evaluated by performing a direct extraction of an aqueous matrix containing 40 ppm of DBBP. They were subsequently applied to the direct extraction of DBBP from an aqueous matrix that contained 40 ppm BTEX compounds as an interference. The results of the extractions from the solutions containing only DBBP for the SPME fibers that were pyrolyzed at 400, 600, and 800° C. are shown in FIGS. 5, 6, and 7, respectively. The equilibration profiles for the extraction of DBBP from the solution containing BTEX compounds are illustrated in FIGS. 8-10.

FIG. 5 clearly illustrates that the MI-400° C. SPME fiber extracted more DBBP from an aqueous solution than the non-imprinted 400° C. fiber at equilibrium. Equilibrium for both fibers was achieved at approximately 60 minutes. FIGS. 6 and 7 shows that the MI-600° C. and MI-800° C. fibers both extract more DBBP than their non-imprinted counterparts. The equilibrium times for each of these fibers are approximately 30 minutes. The total amount of DBBP extracted appeared to decrease with increasing pyrolyzation temperature which is similar to what we have observed in the past in that the total amount of phase on the fiber decreases with processing temperature. Among the imprinted fibers, the MI-400° C. fiber extracted more than the MI-600° C. fiber. The MI-800° C. extracted the least amount of DBBP. The trend was maintained amongst the non-imprinted fibers as the non-imprinted 400° C. fiber extracted the most DBBP and the least amount of DBBP was extracted by the non-imprinted 800° C. fiber. Also, the selectivity toward the imprinted fiber was higher for the 600° C. compared to the other processing temperatures.

Figure 8A:
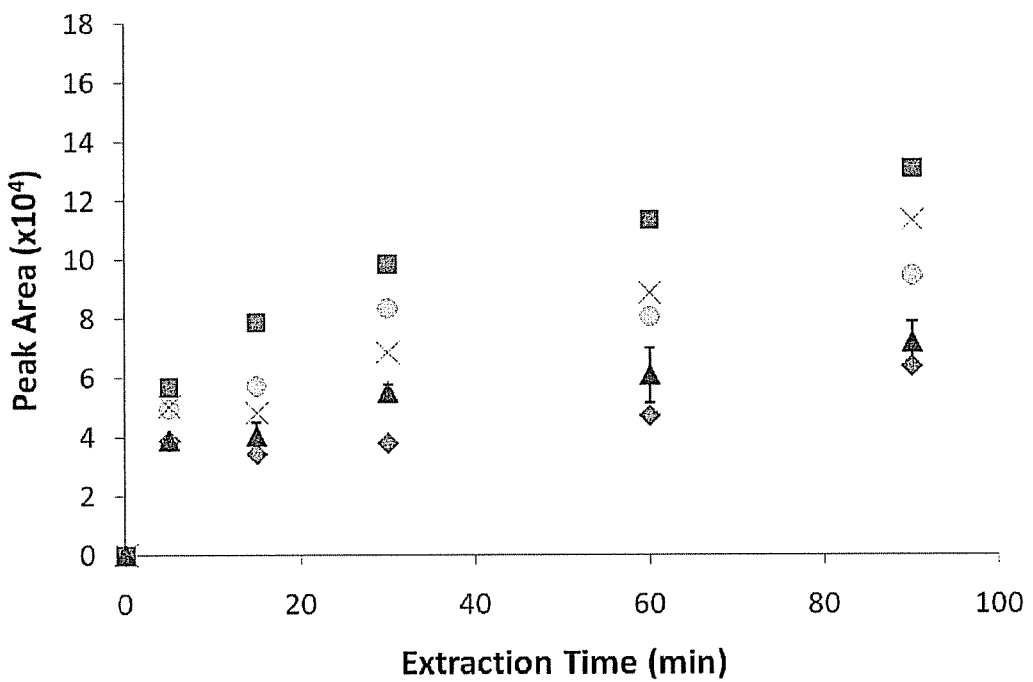
FIG. 8A provides a graph showing the extraction efficiency versus time profiles for the direct extraction of 40 ppm DBBP (▲) in an aqueous matrix containing 40 ppm of benzene (♦), toluene (●), ethylbenzene (■), and o-xylene (X) with an electrospun MI-400° C. SPME fiber. Constant stirring at room temperature, stirring speed set to 50% of maximum. GC conditions: 30° C. for 1 min, then programmed at 5° C./min to 100° C., 12° C./min to 140° C., and 2° C./min to 190° C.; inlet temperature set at 300° C. and detector temperature set at 300° C.
Figure 8B:
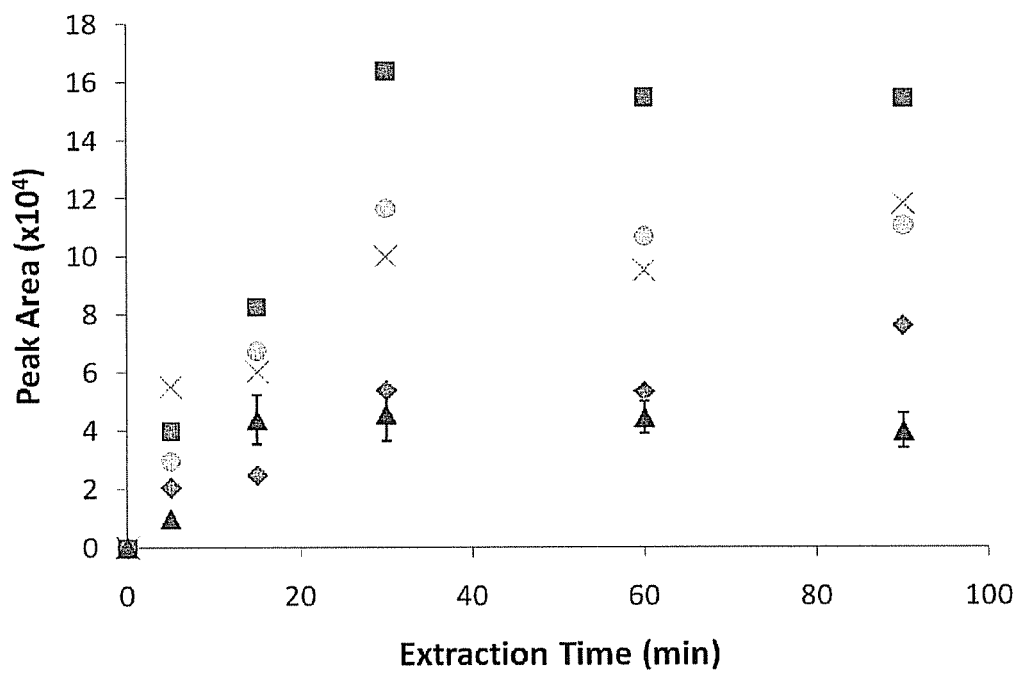
FIG. 8B provides a graph showing the extraction efficiency versus time profiles for the direct extraction of 40 ppm DBBP (▲) in an aqueous matrix containing 40 ppm of benzene (♦), toluene (●), ethylbenzene (■), and o-xylene (X) with an electrospun non-imprinted 400° C. SPME fiber. Constant stirring at room temperature, stirring speed set to 50% of maximum. GC conditions: 30° C. for 1 min, then programmed at 5° C./min to 100° C., 12° C./min to 140° C., and 2° C./min to 190° C.; inlet temperature set at 300° C. and detector temperature set at 300° C.
Figure 8C:
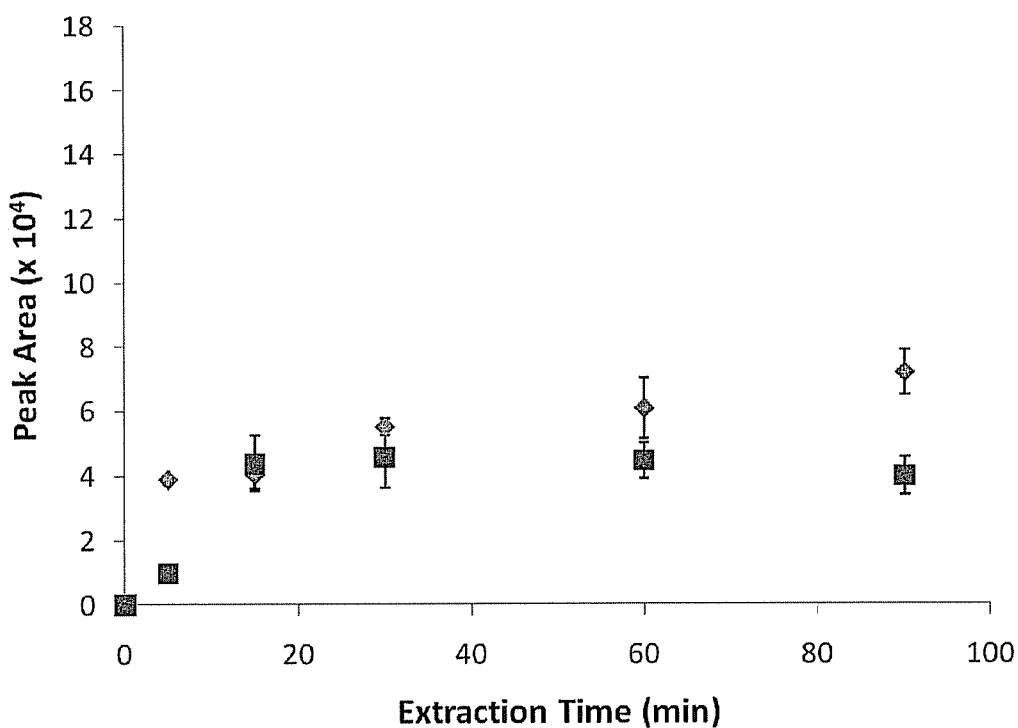
FIG. 8C provides a graph comparing the amount of DBBP extracted by the electrospun MI-400° C. SPME fiber (♦) and the electrospun non-imprinted 400° C. SPME fiber (■) from an aqueous matrix containing 40 ppm of DBBP and BTEX. Constant stirring at room temperature, stirring speed set to 50% of maximum. GC conditions: 30° C. for 1 min, then programmed at 5° C./min to 100° C., 12° C./min to 140° C., and 2° C./min to 190° C.; inlet temperature set at 300° C. and detector temperature set at 300° C.

The performance of the MI-400° C. in extracting DBBP from an aqueous solution also containing BTEX is illustrated in FIG. 8A. Ethylbenzene was the most extracted analyte and equilibrium was reached at approximately 60 minutes. FIG. 8B shows the equilibration curves for DBBP and BTEX in an aqueous solution for the non-imprinted 400° C. fiber. As with the MI-400° C. SPME fiber, ethylbenzene was the most extracted analyte; the equilibration time was approximately 60 minutes. All of the BTEX chemicals were more readily extracted by the non-imprinted 400° C. fiber than the MI-400° C. fiber. FIG. 8B shows a direct comparison of the amount of DBBP extracted for each fiber from aqueous solutions containing BTEX. Once equilibrium is reached, the MI-400° C. fiber extracts more DBBP than the non-imprinted 400° C. fiber.

Figure 9A:
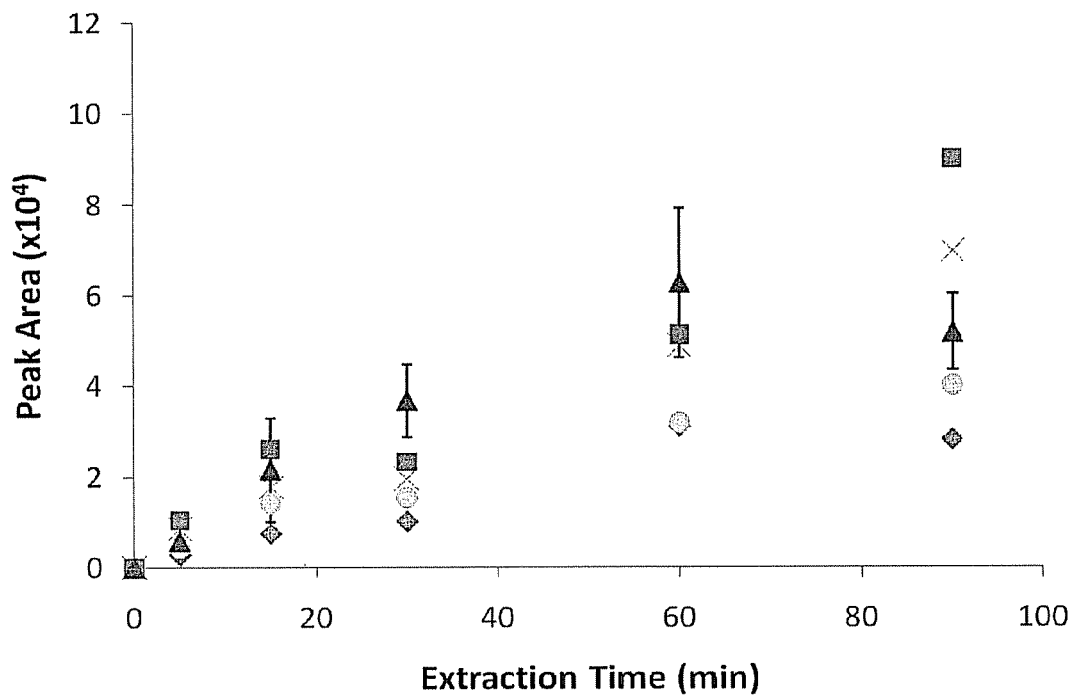
FIG. 9A provides a graph showing the extraction efficiency versus time profiles for the direct extraction of 40 ppm DBBP (▲) in an aqueous matrix containing 40 ppm of benzene (♦), toluene (●), ethylbenzene (■), and o-xylene (X) with an electrospun MI-600° C. SPME fiber. Constant stirring at room temperature, stirring speed set to 50% of maximum. GC conditions: 30° C. for 1 min, then programmed at 5° C./min to 100° C., 12° C./min to 140° C., and 2° C./min to 190° C.; inlet temperature set at 300° C. and detector temperature set at 300° C.
Figure 9B:
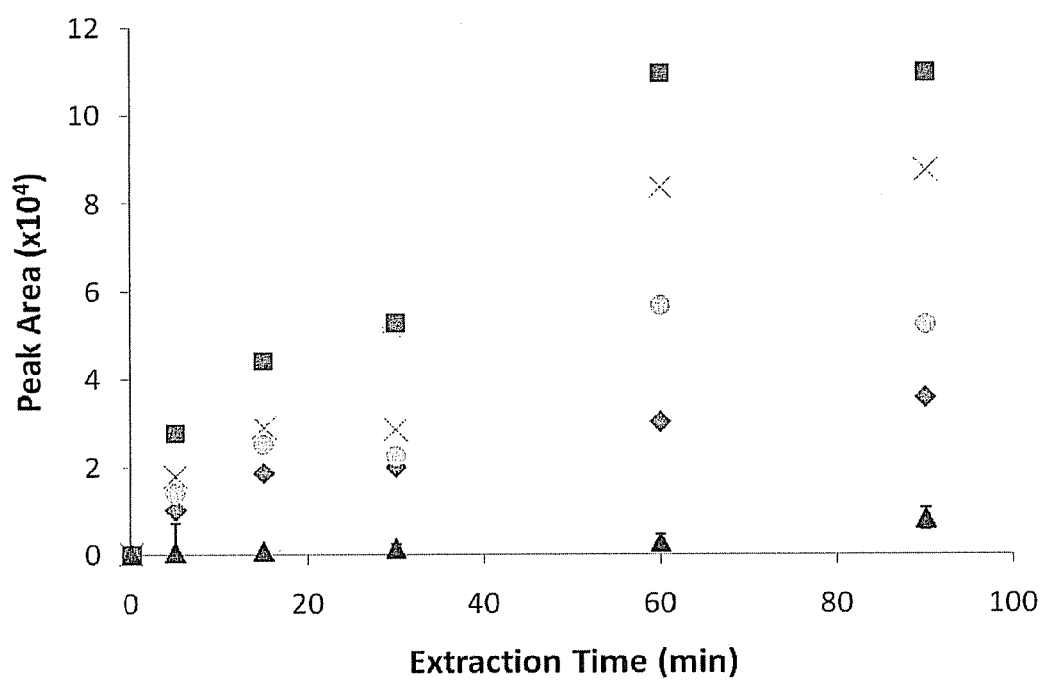
FIG. 9B provides a graph showing the extraction efficiency versus time profiles for the direct extraction of 40 ppm DBBP (▲) in an aqueous matrix containing 40 ppm of benzene (♦), toluene (●), ethylbenzene (■), and o-xylene (X) with an electrospun non-imprinted 600° C. SPME fiber. Constant stirring at room temperature, stirring speed set to 50% of maximum. GC conditions: 30° C. for 1 min, then programmed at 5° C./min to 100° C., 12° C./min to 140° C., and 2° C./min to 190° C.; inlet temperature set at 300° C. and detector temperature set at 300° C.
Figure 9C:
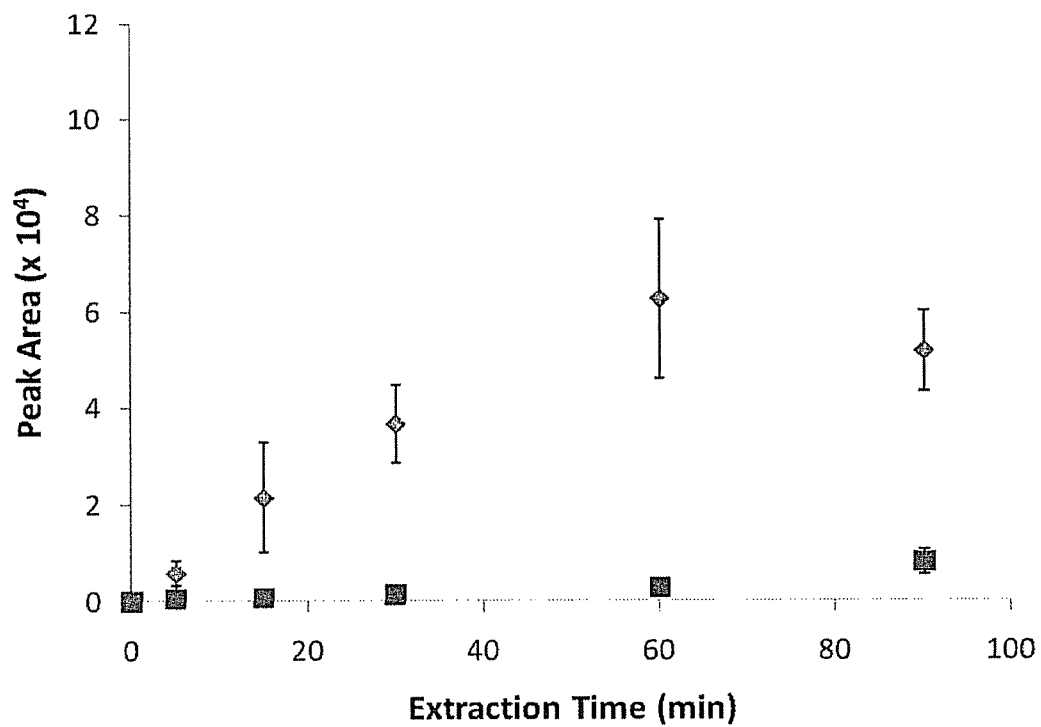
FIG. 9C provides a graph comparing the amount of DBBP extracted by the electrospun MI-600° C. SPME fiber (♦) and the electrospun non-imprinted 600° C. SPME fiber (■) from an aqueous matrix containing 40 ppm of DBBP and BTEX. Constant stirring at room temperature, stirring speed set to 50% of maximum. GC conditions: 30° C. for 1 min, then programmed at 5° C./min to 100° C., 12° C./min to 140° C., and 2° C./min to 190° C.; inlet temperature set at 300° C. and detector temperature set at 300° C.

The equilibration profiles for the extraction of DBBP and BTEX from an aqueous solution for MI-600° C. and non-imprinted 600° C. fibers are shown in FIGS. 9A and 9B, respectively. In both cases, ethylbenzene was once again the most extracted compound, though to a much higher degree regarding the non-imprinted 600° C. fiber. DBBP equilibration was achieved at approximately 60 minutes for the MI-600° C. fiber and 30 minutes for the non-imprinted 600° C. fiber. However, as shown in FIG. 9C, the MI-600° C. extracted much more DBBP than the non-imprinted 600° C. fiber. Compared to FIG. 6, which showed the extraction of DBBP without competition for both MI and non-imprinted 600° C. fibers, the amount of DBBP extracted was equivalent for the MI-600° C. fiber. Competition appeared to have a more negative impact on the extraction of DBBP for the non-imprinted 600° C. fiber.

Figure 10A:
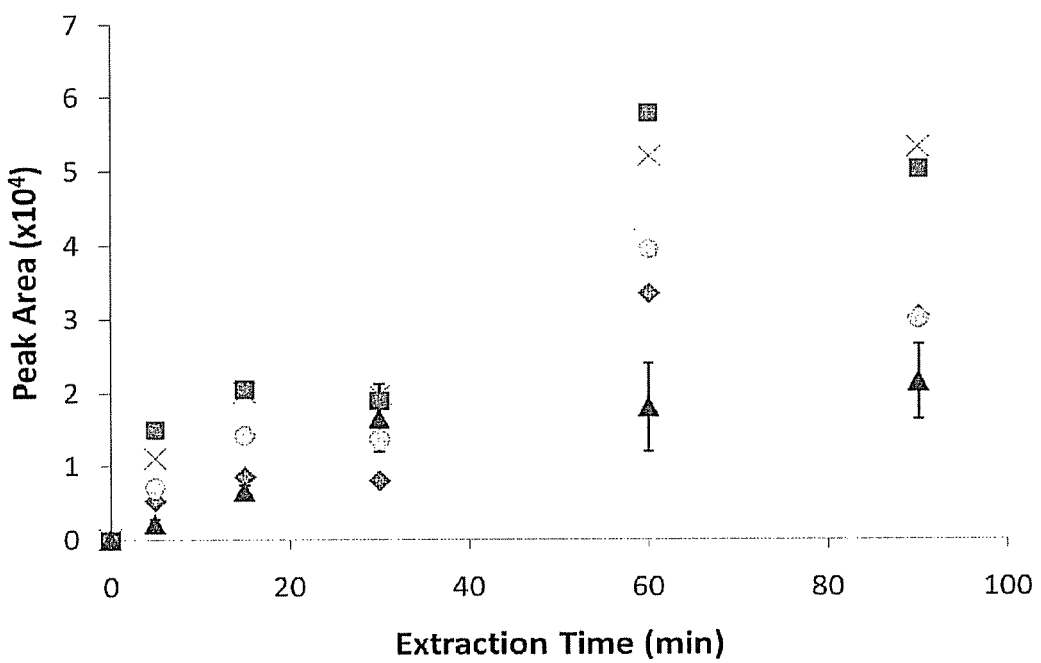
FIG. 10A provides a graph showing the extraction efficiency versus time profiles for the direct extraction of 40 ppm DBBP (▲) in an aqueous matrix containing 40 ppm of benzene (♦), toluene (●), ethylbenzene (■), and o-xylene (X) with an electrospun MI-800° C. SPME fiber. Constant stirring at room temperature, stirring speed set to 50% of maximum. GC conditions: 30° C. for 1 min, then programmed at 5° C./min to 100° C., 12° C./min to 140° C., and 2° C./min to 190° C.; inlet temperature set at 300° C. and detector temperature set at 300° C.
Figure 10B:
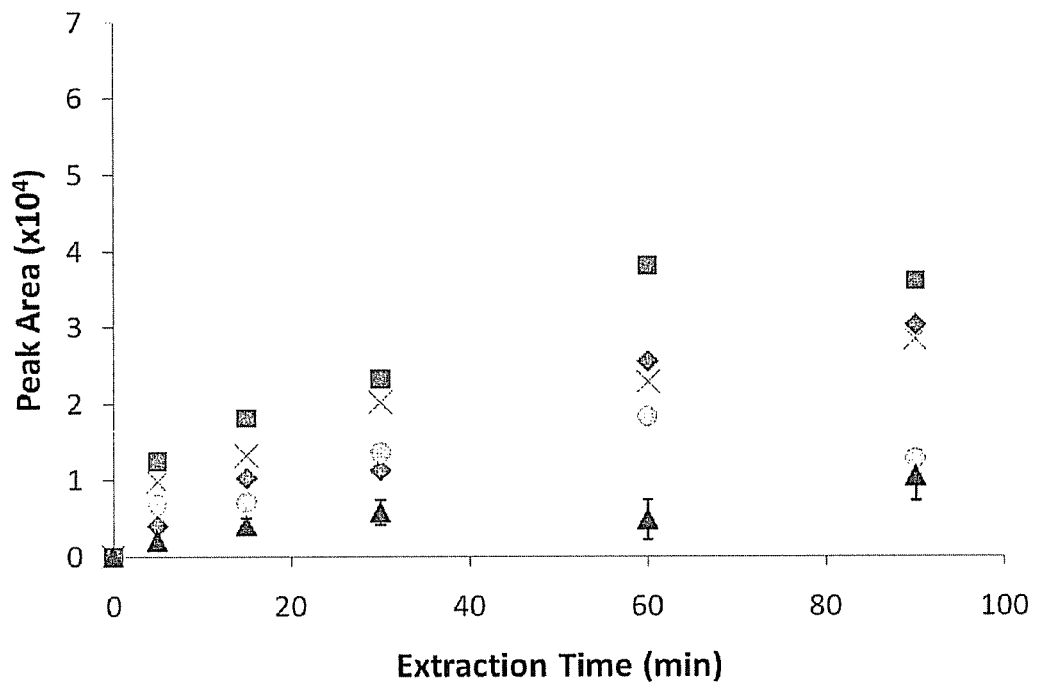
FIG. 10B provides a graph showing the extraction efficiency versus time profiles for the direct extraction of 40 ppm DBBP (▲) in an aqueous matrix containing 40 ppm of benzene (♦), toluene (●), ethylbenzene (■), and o-xylene (X) with an electrospun non-imprinted 800° C. SPME fiber. Constant stirring at room temperature, stirring speed set to 50% of maximum. GC conditions: 30° C. for 1 min, then programmed at 5° C./min to 100° C., 12° C./min to 140° C., and 2° C./min to 190° C.; inlet temperature set at 300° C. and detector temperature set at 300° C.
Figure 10C:
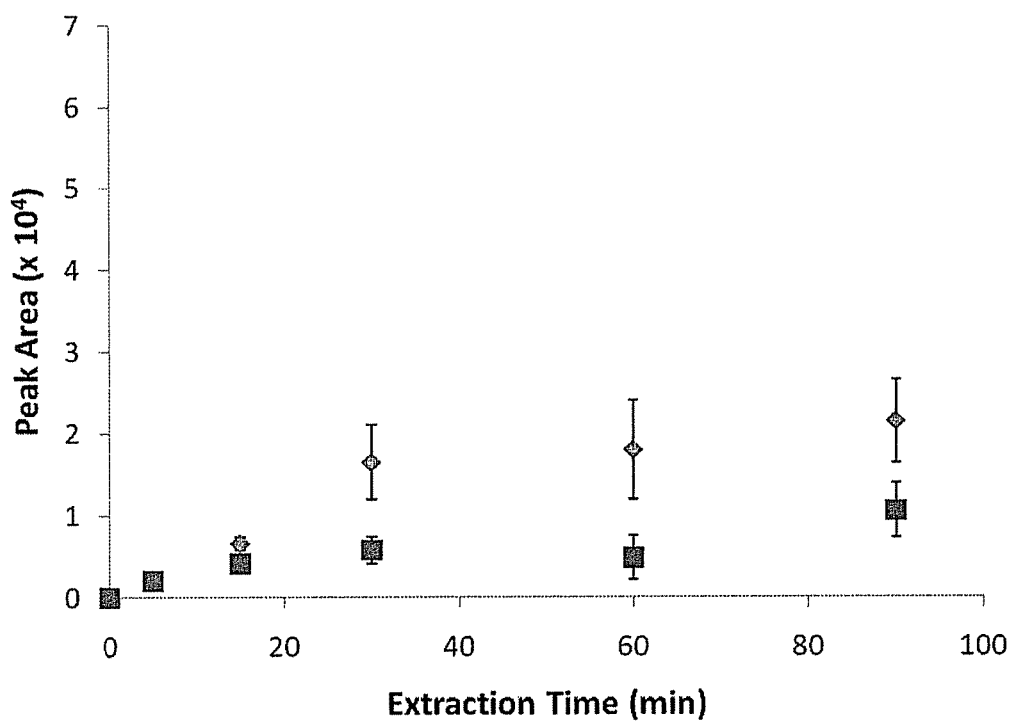
FIG. 10C provides a graph comparing the amount of DBBP extracted by the electrospun MI-800° C. SPME fiber (♦) and the electrospun non-imprinted 800° C. SPME fiber (■) from an aqueous matrix containing 40 ppm of DBBP and BTEX. Constant stirring at room temperature, stirring speed set to 50% of maximum. GC conditions: 30° C. for 1 min, then programmed at 5° C./min to 100° C., 12° C./min to 140° C., and 2° C./min to 190° C.; inlet temperature set at 300° C. and detector temperature set at 300° C.

FIGS. 10A and 10B show the extraction of DBBP and BTEX from an aqueous matrix for the MI-800° C. SPME and the 800° C. SPME, respectively. Equilibration was reached at approximately 60 minutes for both fibers; surprisingly, ethylbenzene remained the most extracted analyte for both fibers as well. Unlike the fibers processed at 400° C. and 600° C., the MI-800° C. fiber extracted the most DBBP and the most BTEX, in the other two cases, the non-imprinted fiber extracted more BTEX relative to its molecularly imprinted counterpart. FIG. 10C compares the two fibers' performance in extracting DBBP from the aqueous BTEX solution; the MI-800° C. showed an improved extraction for DBBP relative to the non-imprinted fiber. Competition appeared to negatively affect both fibers processed to 800° C.; comparing FIG. 10C with FIG. 7, it is clear that both the MI-800° C. fiber and the non-imprinted 800° C. fiber were able to extract more DBBP from an aqueous solution where no BTEX interference was present.

For all processing temperatures, both with and without competition, the amount of extracted DBBP was higher for the MI-PP fibers than for the non-imprinted PP fibers. Furthermore, the MI-PP fibers extracted less BTEX than their non-imprinted counterparts, demonstrating greater selectivity for DBBP. The only fiber for which this was not the case was the MI-800° C. SPME fiber, which extracted both more DBBP and BTEX than the non-imprinted 800° C. SPME fiber. Competition appears to have an effect on the amount of DBBP adsorbed by the fibers; only the MI-600° C. SPME fiber did not exhibit a decrease in the amount of DBBP extracted from the aqueous solution containing BTEX when compared to the equilibration profile from an aqueous solution containing DBBP alone.

Table I shows the improvements in selectivity observed with molecular imprinting of DBBP. Clearly the MI-SPME that had been pyrolyzed at 600° C. shows the highest selectivity when compounds of different chemical structures are competing for surface sites and show significantly increased affinity for the surface in the absence of compounds of other chemical structures.

TABLE I

Selectivity Ratio of MI-SPME relative to non-imprinted SPME

| Material | Ratio of DBBP Extracted by MI-SPME vs. Non-Imprinted SPME without BTEX | Ratio of DBBP Extracted by MI-SPME vs. Non-Imprinted SPME with BTEX |
| --- | --- | --- |
| SU-8 2100 | 1.27 | 1.43 |
| 400° C. PP | 2.00 | 1.43 |
| 600° C. PP | 3.39 | 6.41 |
| 800° C. PP | 3.43 | 2.56 |

Due to its enhanced selectivity, the MI-600° C. SPME fiber was employed in the extraction of DBBP from an aqueous solution containing 40 ppm DBBP as well as 40 ppm dioctyl phenyl phosphonate (DOPP), a compound that is structurally similar to DBBP. The equilibration profile for the MI-600° C. SPME fiber was compared to that of

TABLE II

The amount of DBBP extracted by sorbent phases comprised of electrospun and spin-coated SU-8, MI-SU-8, and 600° C. PP, and MI-600° C. PP. Extractions were performed from 20 mL of saturated aqueous DBBP solution for 24 hours.

| Material | Coating Method | Mass DBBP Extracted (µg/cm$^2$) |
| --- | --- | --- |
| SU-8 2100 | Electrospinning | 5920 |
| | Spin-Coating | 5220 |
| MI-SU-8 2100 | Electrospinning | 6090 |
| | Spin-Coating | 5450 |
| 600° C. PP | Electrospinning | 6420 |
| | Spin Coating | 5040 |
| MI-600° C. PP | Electrospinning | 7750 |
| | Spin-Coating | 6840 | the non-imprinted 600° CSPME fiber for evaluation. These profiles are shown in FIG. 11.

Figure 11:
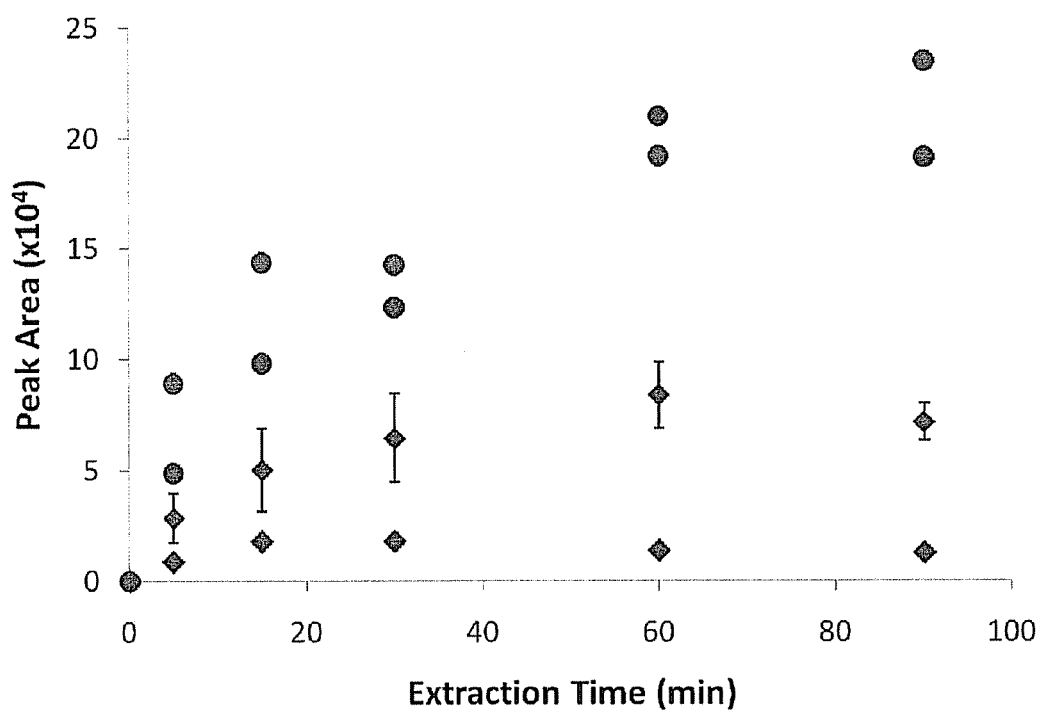
FIG. 11 provides a graph showing the extraction efficiency versus time profiles for the direct extraction of 40 ppm DBBP in an aqueous matrix containing 40 ppm DOPP with electrospun MI-600° C. (DBBP(♦) and DOPP(●)) and non-imprinted 600° C. (DBBP(♦) and DOPP (●)) SPME fibers. Constant stirring at room temperature, stirring speed set to 50% of maximum.

FIG. 11 shows that equilibrium for both fibers was reached at approximately 90 minutes. The amount of DBBP extracted by the MI-600° C. and the non-imprinted 600° C. was comparable to that observed for the extraction of DBBP from an aqueous solution without BTEX. In the case of both fibers the DOPP was more readily extracted than the DBBP. However, the MI-600° C. SPME fiber extracted a significantly larger amount of DBBP and a slightly larger amount of DOPP than the non-imprinted 600° C. fiber at equilibrium. This may suggest that, while the imprint is more discriminating for DBBP, the phosphonate group contained within DOPP may also show a slight affinity for the molecularly imprinted surface, though to a much smaller extent.

Importance of Electrospinning to Molecular Imprintings

Solid phase extractions were performed to determine if the electrospinning process influenced the imprinting process of DBBP. MI-SU-8 and non-imprinted SU-8 and MI-600° C. PP surfaces were generated based on both electrospinning of nanofibers and spin coating of continuous films onto silicon chips. These chips were placed in a 20 mL, saturated aqueous solution of DBBP for a 24 hour extraction. Following the extraction, the concentration of DBBP remaining in the solution was determined to find the amount of DBBP extracted by the electrospun and spin-coated phases. Table II shows the amount of DBBP extracted by each sorbent.

The SPE data once again show that the MI-SU-8 extracts more DBBP than the non-imprinted polymer. Additionally, the MI-PP extracted a larger mass of DBBP than the MI-SU-8, which is consistent with the findings of the SPME experiments. However, most importantly these data demonstrate that no appreciable difference in imprinting occurs for electrospun imprinted polymer relative to spin-coated imprinted polymer (i.e. the electrospinning is not necessary for the molecular imprinting to occur).

General Use and Fiber Stability

On average, effective lifetime of the SPME fiber coating was found to be 20-30 extractions, with fiber failure frequently occurring due to scraping of the SPME fibers against the side of SPME holder when the fiber was extended and retracted. However, for the MI-SU-8 SPME fibers, it was observed that the preferential selectivity toward DBBP generally faded after 10-15 uses. This is not altogether unexpected, as mentioned previously. However, the MI-PP SPME fibers did not demonstrate such behavior, at any processing temperature, showing preferential extraction of DBBP until fiber failure occurred.

The thickness of the fiber coating was reproducible for both imprinted and non-imprinted fibers, varying no more than 10% between fibers pyrolyzed to the same temperature. No fiber bleed was observed prior to failure for both types of fibers.

Conclusions

The preparation of electrospun MI-SU-8 and MI-PP, using DBBP as a template molecule, was described. All of the extractions performed in this study demonstrated that the electrospun MI-SU-8 and MI-PP SPME fibers demonstrated enhanced selectivity for the DBBP template molecule versus the non-imprinted SPME fibers. The effect of molecular imprinting was most pronounced in the fibers pyrolyzed at 600° C.; the MI-600° C. SPME fibers extracted approximately four to five times as much DBBP as the non-imprinted 600° C. fibers. All of the MI-PP fibers showed an increase in the amount of DBBP extracted of at least 60%. The MI-SU-8 SPME fiber showed an increase in DBBP extraction of 30-40% relative to its non-imprinted counterpart. These findings were corroborated via solid phase extraction. The MI-SU-8 SPME fibers showed that the molecular imprint degraded with repeated use, and was frequently diminished prior to SPME fiber failure. This was not observed for the MI-PP SPME fibers, which are more thermally stable.

The complete disclosure of all patents, patent applications, and publications, and electronically available materials cited herein are incorporated by reference. The foregoing detailed description and examples have been given for clarity of understanding only. No unnecessary limitations are to be understood therefrom. In particular. any theories of operation presented herein are optional and the inventors are therefore not bound by theories described herein. The invention is not limited to the exact details shown and described, for variations obvious to one skilled in the art will be included within the invention defined by the claims.

What is claimed is:

1. A composition comprising a nongraphitizable molecularly imprinted carbon derived from a molecularly imprinted polymer; wherein a portion of the molecularly imprinted carbon has a shape corresponding to the shape of at least a portion of a template molecule; and wherein the molecularly imprinted carbon has an affinity for the template molecule, wherein the molecularly imprinted carbon is formed by pyrolysis of the molecularly imprinted polymer in an inert or reducing atmosphere.

2. The composition of claim 1, wherein the molecularly imprinted polymer comprises a polymer selected from the group consisting of: cellulose, poly(furfuryl alcohol) or a furfuryl alcohol copolymer, poly(vinylidene chloride), resorcinol-phenol copolymer, highly unsaturated polymers, polyimide, and polyacrylonitrile.

3. The composition of claim 1, wherein the molecularly imprinted polymer comprises a photoresist polymer.

4. The composition of claim 3, wherein the photoresist polymer is an epoxy-based negative photoresist.

5. The composition of claim 4, wherein the polymer is SU-8.

6. The composition of claim 1, wherein the molecularly imprinted polymer is imprinted by the template molecule, wherein the template molecule has a size of 1 micron or less.

7. A solid phase microextraction device comprising a solid support, at least a portion of a surface of the solid support carrying a layer thereon, wherein the layer comprises the composition of claim 1.

8. The composition of claim 1, wherein the molecularly imprinted carbon has greater affinity for the template molecule than does the molecularly imprinted polymer.

9. The composition of claim 1, wherein the composition is a coating.

10. A composition comprising a nongraphitizable molecularly imprinted carbon; wherein a portion of the molecularly imprinted carbon has a shape corresponding to the shape of at least a portion of a template molecule; wherein the molecularly imprinted carbon has an affinity for the template molecule; wherein the nongraphitizable molecularly imprinted carbon is produced by:
 applying a mixture including a cross-linkable base polymer and a template molecule to at least a portion of a surface of a solid support;
 crosslinking the base polymer to form a molecularly imprinted polymer;
 extracting the template molecule from the molecularly imprinted polymer, and
 pyrolyzing the molecularly imprinted polymer in an inert or reducing atmosphere to form the nongraphitizable molecularly imprinted carbon.

11. The device of claim 7, wherein the solid support comprises stainless steel wires.

12. the device of claim 7, wherein the molecularly imprinted carbon has a first portion having a shape corresponding to the shape of at least a portion of a first template molecule, and a second portion having a shape corresponding to at least a portion of a second template molecule.

* * * * *